United States Patent
Loughnane et al.

(10) Patent No.: US 11,241,310 B2
(45) Date of Patent: Feb. 8, 2022

(54) REPLACEMENT HEART VALVE DELIVERY DEVICE

(71) Applicant: BOSTON SCIENTIFIC SCIMED, INC., Maple Grove, MN (US)

(72) Inventors: Declan Loughnane, Galway (IE); Tim O'Connor, Galway (IE); Sean O'Sullivan, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 300 days.

(21) Appl. No.: 16/439,800

(22) Filed: Jun. 13, 2019

(65) Prior Publication Data

US 2019/0380829 A1 Dec. 19, 2019

Related U.S. Application Data

(60) Provisional application No. 62/684,313, filed on Jun. 13, 2018.

(51) Int. Cl.
   *A61F 2/24* (2006.01)
   *A61F 2/95* (2013.01)

(52) U.S. Cl.
   CPC ............ *A61F 2/243* (2013.01); *A61F 2/2439* (2013.01); *A61F 2/2436* (2013.01); *A61F 2002/9505* (2013.01); *A61F 2002/9511* (2013.01)

(58) Field of Classification Search
   None
   See application file for complete search history.

(56) References Cited

U.S. PATENT DOCUMENTS

| 15,192 A | 6/1856 | Peale |
| 2,682,057 A | 6/1954 | Lord |
| 2,701,559 A | 2/1955 | Cooper |
| 2,832,078 A | 4/1958 | Williams |
| 3,029,819 A | 4/1962 | Starks |
| 3,099,016 A | 7/1963 | Lowell |

(Continued)

FOREIGN PATENT DOCUMENTS

| AU | 2002329324 B2 | 7/2007 |
| CN | 1338951 A | 3/2002 |

(Continued)

OTHER PUBLICATIONS

US 8,062,356 B2, 11/2011, Salahieh et al. (withdrawn)

(Continued)

*Primary Examiner* — Shaun L David
(74) *Attorney, Agent, or Firm* — Seager, Tufte & Wickhem LLP

(57) ABSTRACT

A medical device system may include a delivery device including an outer sheath and an inner shaft having a coupler fixed to a distal end of the inner shaft, and a replacement heart valve implant releasably attached to the coupler, the replacement heart valve implant including an expandable anchor member and a plurality of locking mechanisms configured to engage with the coupler. The delivery device may include a plurality of collars configured to secure the coupler to the plurality of locking mechanisms. The delivery device may include a stop element configured to selectively prevent disengagement of the plurality of collars from the plurality of locking mechanisms.

14 Claims, 11 Drawing Sheets

(56) References Cited

U.S. PATENT DOCUMENTS

| | | |
|---|---|---|
| 3,113,586 A | 12/1963 | Edmark |
| 3,130,418 A | 4/1964 | Head et al. |
| 3,143,742 A | 8/1964 | Cromie |
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz et al. |
| 3,409,013 A | 11/1968 | Henry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,739 A | 6/1995 | Jessen |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |
| 5,507,767 A | 4/1996 | Maeda et al. |
| 5,522,881 A | 6/1996 | Lentz |
| 5,534,007 A | 7/1996 | Germain et al. |
| 5,545,133 A | 8/1996 | Burns et al. |

(56) References Cited

U.S. PATENT DOCUMENTS

| | | |
|---|---|---|
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Faheri et al. |
| 5,607,464 A | 3/1997 | Frescony et al. |
| 5,609,626 A | 3/1997 | Quijano et al. |
| 5,628,784 A | 5/1997 | Strecker |
| 5,645,559 A | 7/1997 | Hachtman et al. |
| 5,653,745 A | 8/1997 | Trescony et al. |
| 5,662,671 A | 9/1997 | Barbut et al. |
| 5,667,523 A | 9/1997 | Bynon et al. |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson et al. |
| 6,051,014 A | 4/2000 | Jang |
| 6,059,827 A | 5/2000 | Fenton |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,911 B1 | 3/2001 | Milo |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |

(56) References Cited

U.S. PATENT DOCUMENTS

| | | |
|---|---|---|
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B1 | 1/2003 | Pavcnik et al. |
| 6,527,800 B1 | 3/2003 | McGuckin et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |

(56) References Cited

U.S. PATENT DOCUMENTS

| | | |
|---|---|---|
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lê et al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,696,743 B2 | 4/2014 | Holecek et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,131 B2 | 10/2015 | Yohanan et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |

(56) References Cited

U.S. PATENT DOCUMENTS

| | | |
|---|---|---|
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0019374 A1 | 1/2004 | Hojeibane et al. |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |

(56) References Cited

U.S. PATENT DOCUMENTS

| | | |
|---|---|---|
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goetz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0171456 A1 | 7/2009 | Kveen et al. |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0299462 A1 | 12/2009 | Fawzi et al. |
| 2009/0319037 A1* | 12/2009 | Rowe ............... A61F 2/2436 623/2.11 |
| 2010/0036479 A1 | 2/2010 | Hill et al. |
| 2010/0049313 A1 | 2/2010 | Mon et al. |
| 2010/0082089 A1 | 4/2010 | Quadri et al. |
| 2010/0094399 A1 | 4/2010 | Dorn et al. |
| 2010/0121434 A1 | 5/2010 | Paul et al. |
| 2010/0161045 A1 | 6/2010 | Righini |
| 2010/0185275 A1 | 7/2010 | Richter et al. |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0280495 A1 | 11/2010 | Paul et al. |
| 2010/0298931 A1 | 11/2010 | Quadri et al. |
| 2011/0257735 A1 | 10/2011 | Salahieh et al. |
| 2011/0264196 A1 | 10/2011 | Savage et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2011/0319989 A1* | 12/2011 | Lane ............... A61F 2/2418 623/2.11 |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0179244 A1 | 7/2012 | Schankereli et al. |
| 2012/0197379 A1 | 8/2012 | Laske et al. |
| 2012/0303113 A1 | 11/2012 | Benichou et al. |
| 2012/0303116 A1 | 11/2012 | Gorman et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0079867 A1 | 3/2013 | Hoffman et al. |
| 2013/0079869 A1 | 3/2013 | Straubinger et al. |
| 2013/0096664 A1 | 4/2013 | Goetz et al. |
| 2013/0123757 A1* | 5/2013 | Crisostomo ....... A61M 25/0074 606/1 |
| 2013/0123795 A1* | 5/2013 | Gamarra ............. A61F 2/2436 606/108 |
| 2013/0123796 A1 | 5/2013 | Sutton et al. |
| 2013/0138207 A1 | 5/2013 | Quadri et al. |
| 2013/0158656 A1 | 6/2013 | Sutton et al. |
| 2013/0184813 A1 | 7/2013 | Quadri et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |
| 2015/0012085 A1 | 1/2015 | Salahieh et al. |
| 2015/0073540 A1 | 3/2015 | Salahieh et al. |
| 2015/0073541 A1 | 3/2015 | Salahieh et al. |
| 2015/0127094 A1 | 5/2015 | Salahieh et al. |
| 2016/0045307 A1 | 2/2016 | Yohanan et al. |
| 2016/0067040 A1 | 3/2016 | Agrawal et al. |
| 2016/0143731 A1* | 5/2016 | Backus ............. A61F 2/2412 623/2.17 |
| 2016/0199184 A1 | 7/2016 | Ma et al. |
| 2016/0206423 A1* | 7/2016 | O'Connor ........... A61F 2/243 |
| 2016/0256271 A1* | 9/2016 | Backus ............. A61F 2/2427 |
| 2017/0165066 A1* | 6/2017 | Rothstein .......... A61F 2/2439 |
| 2017/0216029 A1 | 8/2017 | Crowley et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |

(56) References Cited

FOREIGN PATENT DOCUMENTS

| | | |
|---|---|---|
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 0937439 B1 | 9/2003 |
| EP | 1340473 A2 | 9/2003 |
| EP | 1356793 A3 | 3/2004 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1469797 A1 | 10/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| EP | 2749254 B1 | 6/2015 |
| EP | 2926766 A1 | 10/2015 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A1 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |
| WO | 2006027499 A2 | 3/2006 |
| WO | 2005062980 A3 | 5/2006 |
| WO | 2007035471 A2 | 3/2007 |
| WO | 2005102015 A3 | 4/2007 |
| WO | 2006138391 A2 | 4/2007 |
| WO | 2007044285 A2 | 4/2007 |
| WO | 2007058847 A2 | 5/2007 |
| WO | 2007092354 A2 | 8/2007 |
| WO | 2007097983 A2 | 8/2007 |

(56) References Cited

FOREIGN PATENT DOCUMENTS

| | | | |
|---|---|---|---|
| WO | 2007053243 A2 | 9/2007 | |
| WO | 2007033093 A2 | 1/2008 | |
| WO | 2010042950 A2 | 4/2010 | |
| WO | 2010098857 A1 | 9/2010 | |
| WO | 2012116368 A2 | 8/2012 | |
| WO | 2012162228 A1 | 11/2012 | |
| WO | 2013009975 A1 | 1/2013 | |
| WO | 2013028387 A2 | 2/2013 | |
| WO | 2013074671 A1 | 5/2013 | |
| WO | 2013096545 A1 | 6/2013 | |
| WO | 2016126511 A2 | 8/2016 | |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Carpentier-Edwards PERIMOUNT Bioprosthesis (2003).
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "*Mycobacterium* Chelonei Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48: S33-4 (1989).
Maraj et al., Evaluation of Hemolysis in Patients with Prosthetic Heart Valves, Clin. Cardiol. 21, 387-392 (1998).
McKay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Grafts for Aortic Aneurysms: Feasibility Study." Radiology, 170: 1033-1037 (1989).
Moazami et al., "Transluminal Aortic Valve Placement: A Feasibility Study With a Newly Designed Collapsiable Aortic Valve," ASAIO J. vol. 42:5, pp. M383-85 (Sep./Oct. 1996).
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vasc. Surg., 5(6):491-9 (1991).
Pavcnik et al., "Percutaneous Bioprosthetic Venous Valve: A Long-term Study in Sheep." J. of Vascular Surg., 35(3):598-603, Mar. 2002.
Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.

Printz, et al., "Let the Blood Circulate." Sulzer Tech. Rev. 4/99.
U.S. Appl. No. 60/553,945 to White.
Raillat et al., "Treatment of Iliac Artery Stenosis with the Wallstent Endoprothesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc Intervent Radiol. 15: 319-327 (1992).
Schurink et al,. "Stent Attachment Site-related Endoleakage after Stent Graft Treatment: An in vitro study of the effects of graft size, stent type, and atherosclerotic wall changes." J. Vasc. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther. 8:457-464 (2001).
Thompson et al., "Endoluminal stent grafting of the thoracic aorta: Initial experience with the Gore Excluder," Journal of Vascular Surgery, 1163-70 (Jun. 2002).
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. Feb. 9-17, 2004.
Supplemental Search Report from EP Patent Office, EP Application No. 04815634.3, dated Aug. 19, 2011.
Supplemental Search Report from EP Patent Office, EP Application No. 05758878.2, dated Oct. 24, 2011.
Textbook of Interventional Cardiology, 2d Ed., Chapter 75: Percutaneous Expandable Prosthetic Valves (1994).
Stassano, "Mid-term Results of the Valve on Valve Technique for Bioprosthetic failure." European journal of Ccardiothoracic Surgery:vol. 18, 453-457, Oct. 2000.
Topol, "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109: 1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).
USPTO Case IPR2016-_, U.S. Pat. No. 8,992,608 "Petition for Interpartes Review of U.S. Pat. No. 8,992,608" Oct. 12, 2016.
USPTO Case IPR 2017-0006, U.S. Pat. No. 8,992,608 B2, "Final Written Decision" Mar. 23, 2018.
Fluency Vascular Stent Graft Instructions for Use (2003).
International Search Report and Written Opinion dated Aug. 21, 2019 for International Application No. PCT/US2019/036906.
Cribier et al., "Percutaneous Transluminal Valvuloplasty of Acquired Aortic Stenosis in Elderly Patients: An Alternative to Valve Replacement?" The Lancet, 63-7 (Jan. 11, 1986).

(56) References Cited

OTHER PUBLICATIONS

Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstract)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502 Technical Design Report. Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent—Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356, 1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll, of Cardio, 43(4): 698-703, Feb. 18, 2004.

Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044 1046, May 1979.
Dake et al., "Transluminal Placement of Endovascular Stent-Grafts for the Treatment of Descending Thoracic Aortic Aneurysms." New Engl. J of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000, 12th International Conference Sept. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ng, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).
Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).

\* cited by examiner

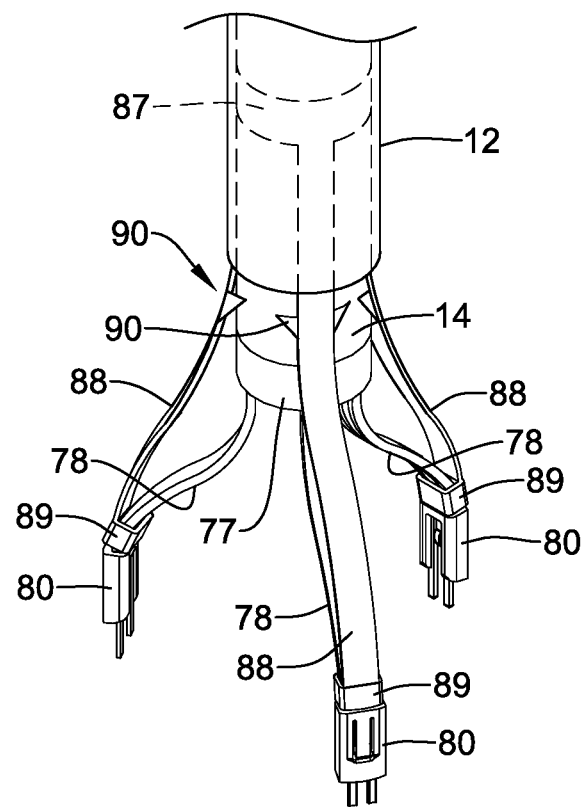
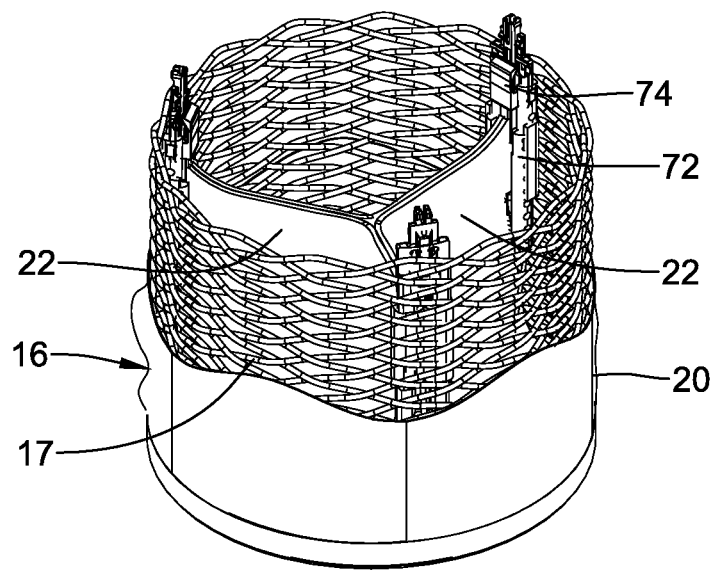
FIG. 9

REPLACEMENT HEART VALVE DELIVERY DEVICE

CROSS-REFERENCE TO RELATED APPLICATIONS

This application claims the benefit of priority under 35 U.S.C. § 119 to U.S. Provisional Application Ser. No. 62/684,313, filed Jun. 13, 2018, the entirety of which is incorporated herein by reference.

TECHNICAL FIELD

The present disclosure pertains to medical devices, and methods for manufacturing and/or using medical devices. More particularly, the present disclosure pertains to a delivery device for a replacement heart valve implant.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a medical device system may comprise a delivery device including an outer sheath and an inner shaft having a coupler fixed to a distal end of the inner shaft; and a replacement heart valve implant releasably attached to the coupler, the replacement heart valve implant including an expandable anchor member and a plurality of locking mechanisms configured to engage with the coupler. The delivery device may include a plurality of collars configured to secure the coupler to the plurality of locking mechanisms. The delivery device may include a stop element configured to selectively prevent disengagement of the plurality of collars from the plurality of locking mechanisms.

In addition or alternatively, and in a second aspect, the coupler includes a proximal ring fixed to the distal end of the inner shaft and a plurality of fingers extending distally from the proximal ring.

In addition or alternatively, and in a third aspect, the stop element includes a proximal band slidably disposed about the inner shaft proximal of the distal end of the inner shaft and a plurality of arms extending distally from the proximal band. Each of the plurality of arms may include a distal loop disposed at a distal end of its respective arm, each distal loop being slidably engaged with one of the plurality of fingers.

In addition or alternatively, and in a fourth aspect, at least one of the plurality of arms includes a wing element configured to selectively engage with the proximal ring of the coupler.

In addition or alternatively, and in a fifth aspect, engagement of the wing element with the proximal ring of the coupler prevents proximal sliding movement of each distal loop with respect to the plurality of fingers.

In addition or alternatively, and in a sixth aspect, the plurality of arms is self-biased radially outward from the inner shaft.

In addition or alternatively, and in a seventh aspect, a proximal portion of the plurality of arms is configured to shift radially relative to the inner shaft between an engagement position and a disengagement position.

In addition or alternatively, and in an eighth aspect, in the engagement position, the proximal portion of the plurality of arms is disposed adjacent to an outer surface of the inner shaft, and in the disengagement position, the proximal portion of the plurality of arms is spaced radially outward from the outer surface of the inner shaft.

In addition or alternatively, and in a ninth aspect, in the engagement position, the proximal portion of the plurality of arms is disposed generally parallel to an outer surface of the inner shaft, and in the disengagement position, the proximal portion of the plurality of arms extends radially outward from the outer surface of the inner shaft at an oblique angle.

In addition or alternatively, and in a tenth aspect, the outer sheath urges the proximal portion of the plurality of arms toward the engagement position when a distal end of the outer sheath is a disposed over the proximal portion of the plurality of arms.

In addition or alternatively, and in an eleventh aspect, proximal retraction of the outer sheath relative to the proximal band permits the proximal portion of the plurality of arms to shift toward the disengagement position.

In addition or alternatively, and in a twelfth aspect, a medical device system may comprise a delivery device including a handle having an outer shell and an interior space, an outer sheath, and an inner shaft having a coupler fixed to a distal end of the inner shaft; wherein a proximal end of the outer sheath and a proximal end of the inner shaft are each operably connected to an axial translation mechanism within the outer shell of the handle, the axial translation mechanism being configured to move to the outer sheath relative to the inner shaft; and a replacement heart valve implant releasably attached to the coupler, the replacement heart valve implant including an expandable anchor member and a plurality of locking mechanisms configured to engage with the coupler. The delivery device may include a plurality of collars configured to secure the coupler to the plurality of locking mechanisms. The delivery device may include a stop element configured to selectively prevent disengagement of the plurality of collars from the plurality of locking mechanisms.

In addition or alternatively, and in a thirteenth aspect, the medical device system may further comprise a locking pin shiftable between a first configuration and a second configuration, wherein the locking pin may extend through an outer wall of the outer shell of the handle in the first configuration, and wherein the locking pin is removed from the outer shell of the handle in the second configuration.

In addition or alternatively, and in a fourteenth aspect, in the first configuration, the locking pin in configured to prevent proximal translation of the outer sheath relative to the stop element.

In addition or alternatively, and in a fifteenth aspect, in the second configuration, proximal translation of the outer sheath relative to the stop element is permitted.

In addition or alternatively, and in a sixteenth aspect, a medical device system may comprise a delivery device including an outer sheath and an inner shaft having a coupler fixed to a distal end of the inner shaft, wherein the coupler includes a proximal ring fixed to the distal end of the inner shaft and a plurality of fingers extending distally from the proximal ring; and a replacement heart valve implant releasably attached to the coupler, the replacement heart valve implant including an expandable anchor member and a plurality of locking mechanisms configured to engage with the plurality of fingers. The delivery device may include a plurality of collars, wherein one collar is slidably disposed on each of the plurality of fingers and is configured to maintain engagement of its respective finger with one of the plurality of locking mechanisms in an interlock position. The delivery device may include a stop element configured to selectively prevent disengagement of the plurality of locking mechanisms from the plurality of fingers by maintaining the plurality of collars in the interlock position when the stop element is engaged with the proximal ring of the coupler.

In addition or alternatively, and in a seventeenth aspect, proximal retraction of the outer sheath relative to the stop element permits the stop element to disengage the proximal ring of the coupler.

In addition or alternatively, and in an eighteenth aspect, when the stop element is disengaged from the proximal ring of the coupler, the plurality of collars is slidable relative to the plurality of fingers to a release position.

In addition or alternatively, and in a nineteenth aspect, the stop element is disposed proximal of the replacement heart valve implant.

In addition or alternatively, and in a twentieth aspect, the stop element does not extend into or through any portion of the replacement heart valve implant.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which:

FIG. 9 is a perspective view of selected elements of the medical device system in the released configuration and/or the disengagement position.

Figure 1:
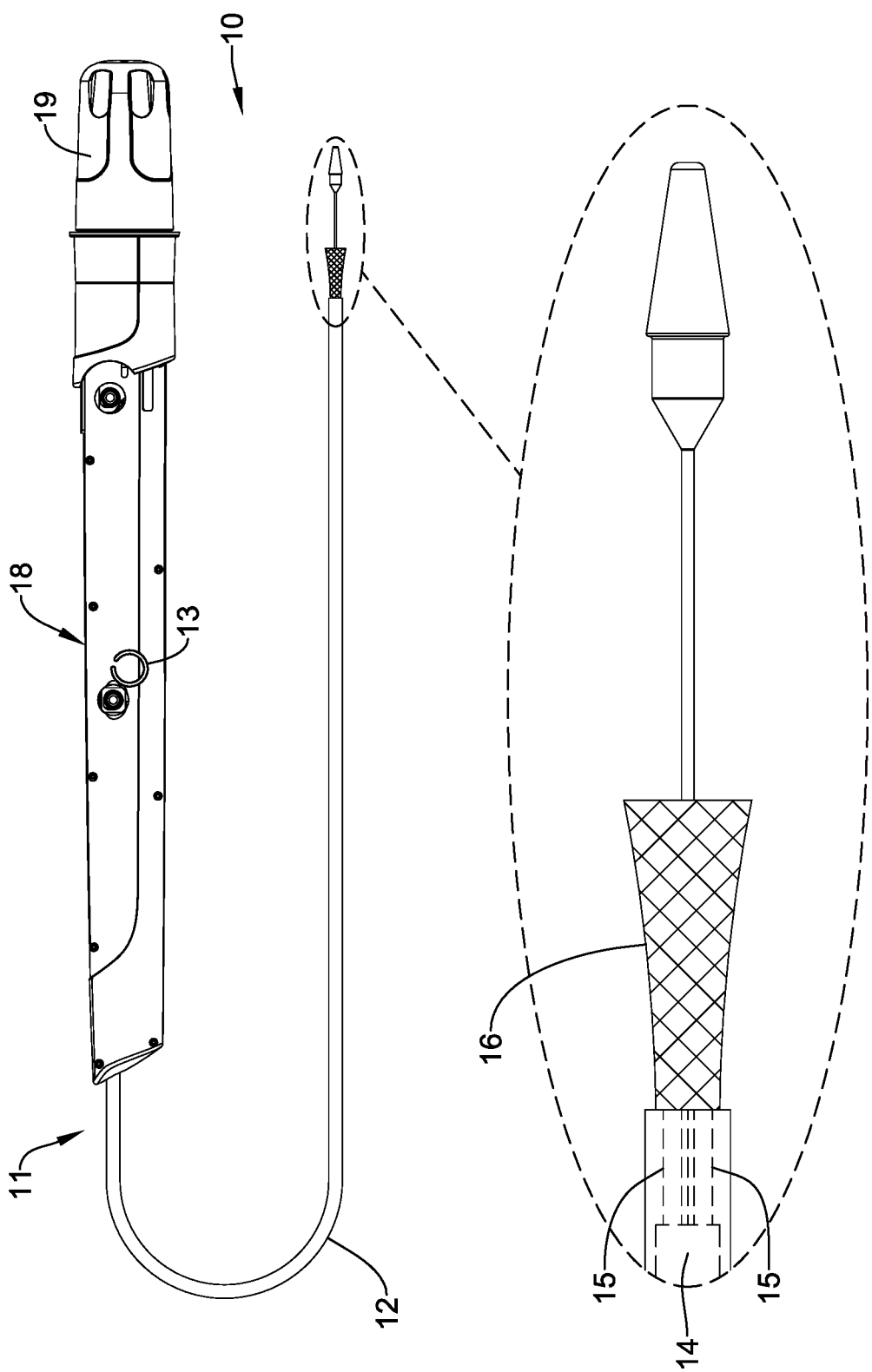
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein is a medical device system that may be used for delivering a medical device to a portion of the cardiovascular system in order to diagnose, treat, and/or repair the system. At least some of the medical devices disclosed herein may be used to deliver and implant a replacement heart valve implant (e.g., a replacement aortic valve, replacement mitral valve, etc.). In addition, the medical device system disclosed herein may deliver the replacement heart valve implant percutaneously and, thus, may be much less invasive to the patient. The device and/or system disclosed herein may also provide other desirable features and/or benefits as described below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices and/or implants to one or more locations within the anatomy. In at least some embodiments, the medical device system 10 may include a delivery device 11 (e.g., a replacement aortic valve delivery system) that can be used for percutaneous delivery of a replacement heart valve implant 16 (e.g., a replacement mitral valve, a replacement aortic valve, etc.) to an area of interest in the anatomy, such as a native heart valve. This, however, is not intended to be limiting as the medical device system 10 and/or the delivery device 11 may also be used for other interventions including valve repair, valvuloplasty, and the like, or other similar interventions.

FIG. 1 illustrates the medical device system 10 including the replacement heart valve implant 16 configured to be disposed within the area of interest, such as a native heart valve (e.g., a mitral valve, an aortic valve, etc.), wherein the replacement heart valve implant 16 may be disposed within a lumen of the delivery device 11 in a delivery configuration for delivery to the area of interest, where the replacement heart valve implant 16 may be shifted to a deployed configuration. In some embodiments, the delivery device 11 may include an outer sheath 12 having a lumen extending from a proximal portion and/or proximal end of the outer sheath 12 to a distal end of the outer sheath 12. The replacement heart valve implant 16 may be disposed within the lumen of the outer sheath 12 proximate the distal end of the outer sheath 12 in the delivery configuration. In some embodiments, the delivery device 11 may include a handle 18 disposed proximate and/or at the proximal end of the outer sheath 12. The handle 18 may have an outer shell and an interior space. In some embodiments, the handle 18 may have a control knob 19.

The delivery device 11 may include an inner shaft or catheter 14 disposed within the lumen of the outer sheath 12 and/or slidable with respect to the outer sheath 12 within the lumen of the outer sheath 12. In some embodiments, the handle 18 may be disposed proximate and/or at a proximal end of the inner shaft or catheter 14. In some embodiments, the inner shaft or catheter 14 may be a tubular structure having one or more lumens extending therethrough, the inner shaft or catheter 14 may be a solid shaft, or the inner shaft or catheter 14 may be a combination thereof. In some embodiments, the proximal end of the outer sheath 12 and the proximal end of the inner shaft or catheter 14 may each be operably connected, fixed, and/or secured to an axial translation mechanism disposed within the outer shell of the handle 18. The axial translation mechanism may be configured to move and/or translate the outer sheath 12 relative to the inner shaft or catheter 14.

In some embodiments, the delivery device 11 may include an actuator element 15 releasably connecting the replacement heart valve implant 16 to the handle 18. For example, the actuator element 15 may extend from the handle 18 to the replacement heart valve implant 16, the replacement heart valve implant 16 being disposed at a distal end of the lumen of the outer sheath 12. The actuator element 15 may extend distally from the inner shaft or catheter 14 to the replacement heart valve implant 16. In some embodiments, the actuator element 15 may be slidably disposed within and/or may extend slidably through the inner shaft or catheter 14.

The handle 18 and/or the actuator element 15 may be configured to manipulate the position of the outer sheath 12 relative to the inner shaft or catheter 14 and/or aid in the deployment of the replacement heart valve implant 16. For example, the inner shaft or catheter 14 and/or the actuator element 15 may be used to move the replacement heart valve implant 16 with respect to the outer sheath 12 of the delivery device 11. In some embodiments, the inner shaft or catheter 14 and/or the actuator element 15 may be advanced distally within the lumen of the outer sheath 12 to push the replacement heart valve implant 16 out the distal end of the outer sheath 12 and/or the delivery device 11 to deploy the replacement heart valve implant 16 within the area of interest (e.g., the native heart valve, etc.). In some embodiments, the inner shaft or catheter 14 and/or the actuator element 15 may be held in a fixed position relative to the replacement heart valve implant 16 and the outer sheath 12 may be withdrawn proximally relative to the inner shaft or catheter 14, the actuator element 15, and/or the replacement heart valve implant 16 to deploy the replacement heart valve implant 16 within the area of interest (e.g., the native heart valve, etc.). A locking pin 13 may be shiftable between a first configuration and a second configuration, wherein the locking pin 13 may extend into the handle 18 through an outer wall of the outer shell of the handle 18 in the first configuration and the locking pin 13 is removed from the outer shell of the handle 18 in the second configuration. In the first configuration, the locking pin 13 may be configured to limit proximal movement and/or translation of the outer sheath 12 relative to the inner shaft or catheter 14 and/or a stop element 86 (e.g., FIG. 2) when the locking pin 13 is in the first configuration and/or extends into the handle 18. In the second configuration, proximal movement and/or translation of the outer sheath 12 relative to the inner shaft or catheter 14 and/or the stop element 86 may be permitted.

The outer sheath 12 may be movable with respect to the inner shaft or catheter 14 between a first position (e.g., FIGS. 2 and 10), wherein a distal end of the outer sheath 12 extends at least to and/or past a distal end of the inner shaft or catheter 14, and a second position (e.g., FIGS. 6 and 11), wherein the distal end of the outer sheath 12 is disposed proximal of the distal end of the inner shaft or catheter 14. Removal of the locking pin 13 may permit the outer sheath 12 to shift from the first position relative to the inner shaft or catheter 14 to the second position relative to the inner shaft or catheter 14. In some embodiments, the outer sheath 12 may be prevented from shifting to the second position relative to the inner shaft or catheter 14 when the locking pin 13 is in place and/or extends into the handle 18. In some embodiments, the second position is at least 0.250 inches proximal of the first position (e.g., the distal end of the outer sheath 12 is at least 0.250 inches proximal of the distal end of the inner shaft or catheter 14). In some embodiments, the second position is at least 0.375 inches proximal of the first position (e.g., the distal end of the outer sheath 12 is at least 0.375 inches proximal of the distal end of the inner shaft or catheter 14). In some embodiments, the second position is at least 0.500 inches proximal of the first position (e.g., the distal end of the outer sheath 12 is at least 0.500 inches proximal of the distal end of the inner shaft or catheter 14). In some embodiments, the second position is at least 0.750 inches proximal of the first position (e.g., the distal end of the outer sheath 12 is at least 0.750 inches proximal of the distal end of the inner shaft or catheter 14), or more. Some examples of suitable but non-limiting materials for the medical device system 10, the delivery device 11, the outer sheath 12, the locking pin 13, the inner shaft or catheter 14, the actuator element 15, the handle 18, and/or components or elements thereof, are described below.

In some embodiments, the delivery device 11 may include a nose cone disposed at a distal end of a guidewire extension tube, wherein the guidewire extension tube may extend distally from the shaft sheath or catheter 14 and/or the outer sheath 12. In at least some embodiments, the nose cone may be designed to have an atraumatic shape and/or may include a ridge or ledge that is configured to abut a distal end of the outer sheath 12 during delivery of the replacement heart valve implant 16.

In use, the medical device system 10 and/or the delivery device 11 may be advanced percutaneously through the vasculature to the area of interest. For example, the medical device system 10 and/or the delivery device 11 may be advanced over a guidewire through the vasculature and across the aortic arch to a defective heart valve (e.g., aortic valve, mitral valve, etc.). Alternative approaches to treat a defective heart valve are also contemplated with the medical device system 10 and/or the delivery device 11. During delivery, the replacement heart valve implant 16 may be generally disposed in an elongated and low profile "delivery" configuration within the lumen of the outer sheath 12. Once positioned, the outer sheath 12 may be retracted relative to the replacement heart valve implant 16 and/or the inner shaft or catheter 14 to expose the replacement heart valve implant 16. In at least some embodiments, the replacement heart valve implant 16 may be disposed in an "everted" configuration or a partially-everted configuration while disposed within the lumen of the outer sheath 12 and/or immediately upon exposure after retracting the outer sheath 12. In some embodiments, the replacement heart valve implant 16 may be everted in the "delivery" configuration. The "everted" configuration may involve at least a portion of the valve leaflets (discussed below) of the replacement heart valve implant 16 being disposed outside of the expandable anchor member (discussed below) of the replacement heart valve implant 16 during delivery, thereby permitting a smaller radial profile of the replacement heart valve implant 16 and the use of a smaller overall profile of the outer sheath 12, the delivery device 11, and/or the medical device system 10. In some embodiments, the "delivery" configuration and the "everted" configuration may be substantially similar and/or may be used interchangeably herein.

The replacement heart valve implant 16 may be actuated using the handle 18 and/or the actuator element 15 in order to translate the replacement heart valve implant 16 into a radially expanded and larger profile "deployed" configuration suitable for implantation within the anatomy at the area of interest or the target location. The replacement heart valve implant 16 may be actuated from the "delivery" configuration to the "deployed" configuration with the locking pin 13 in place and/or extending into the handle 18. After verifying placement of the replacement heart valve implant 16 using a suitable imaging technique, the locking pin 13 may be removed, and the handle 18 may be subsequently actuated to shift the replacement heart valve implant 16 into a "released" configuration. When the replacement heart valve implant 16 is suitably deployed and released within the anatomy, the outer sheath 12 and/or the delivery device 11 can be removed from the vasculature. In at least some interventions, the replacement heart valve implant 16 may be deployed within the native heart valve (e.g., the native heart valve is left in place and not excised). Alternatively, the native heart valve may be removed and the replacement heart valve implant 16 may be deployed in its place as a replacement.

Disposed within a first lumen of the inner shaft or catheter 14 may be the actuator element 15, which may be used to actuate and/or translate (e.g., expand and/or elongate) the replacement heart valve implant 16 between the "delivery" configuration and the "deployed" configuration. In some embodiments, the actuator element 15 may include or comprise a plurality of actuator elements 15, two actuator elements 15, three actuator elements 15, four actuator elements 15, or another suitable or desired number of actuator elements 15. In some embodiments, each actuator element 15 may be disposed within a separate lumen of the inner shaft or catheter 14. For the purpose of illustration only, the medical device system 10, the delivery device 11, and the replacement heart valve implant 16 are shown with three actuator elements 15. In such an example, the three actuator elements 15 may be disposed within three separate lumens (e.g., a first lumen, a second lumen, and a third lumen) of the inner shaft or catheter 14, although such a configuration is not required.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element" may be equally referred to all instances and quantities beyond one of "the at least one actuator element" or "the plurality of actuator elements".

Figure 2:
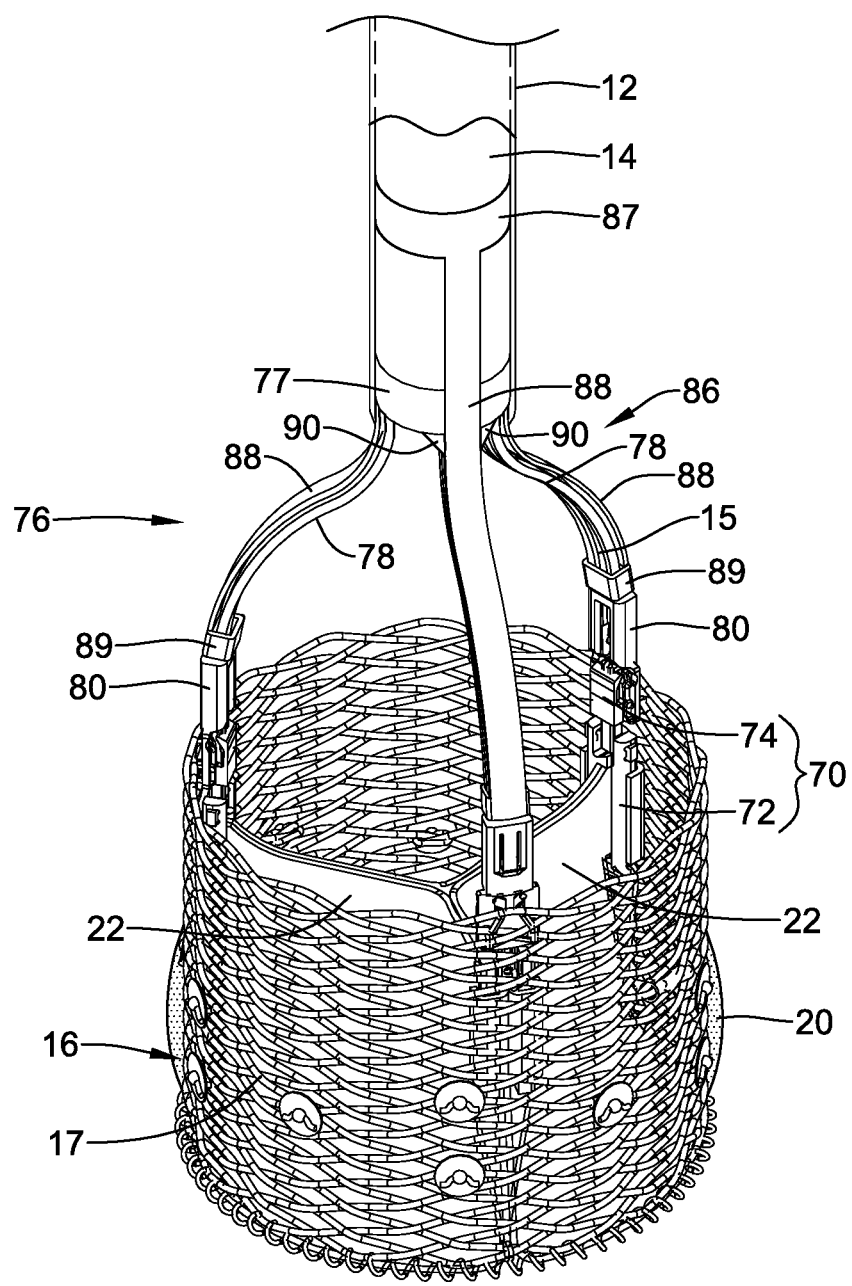
FIG. 2 is a perspective view of selected elements of the medical device system in a deployed configuration and/or an engagement position.

FIG. 2 illustrates some selected components of the medical device system 10, the delivery device 11, and/or the replacement heart valve implant 16, shown in the "deployed" configuration. The replacement heart valve implant 16 may include an expandable anchor member 17 that is reversibly actuatable between the elongated "delivery" configuration and the radially expanded and/or axially shortened "deployed" configuration. In some embodiments, the expandable anchor member 17 may be tubular and defines a lumen extending coaxially along a central longitudinal axis from a distal or inflow end of the expandable anchor member 17 and/or the replacement heart valve implant 16 to a proximal or outflow end of the expandable anchor member 17 and/or the replacement heart valve implant 16.

In some embodiments, the expandable anchor member 17 may comprise an expandable stent structure and/or framework. In some embodiments, the expandable anchor member 17 may comprise a self-expanding braided and/or woven mesh structure made up of one or more filaments disposed and/or interwoven circumferentially about the lumen of the expandable anchor member 17 and/or the replacement heart valve implant 16. Non-self-expanding, mechanically-expandable, and/or assisted self-expanding expandable anchor members are also contemplated. In at least some embodiments, the expandable anchor member 17 may be formed as a unitary structure (e.g., formed from a single filament or strand of wire, cut from a single tubular member, etc.). In some embodiments, the expandable anchor member 17 may define a generally cylindrical outer surface in the deployed configuration. Other configurations are also possible—a cross-section defining a generally elliptical outer surface, for example. Some examples of suitable but non-limiting materials for the replacement heart valve implant 16, the expandable anchor member 17, and/or components or elements thereof, are described below.

Also shown in FIG. 2, but omitted from several other figures in the interest of clarity, the replacement heart valve implant 16 may include a plurality of valve leaflets 22 disposed within the lumen of the replacement heart valve implant 16 and/or the expandable anchor member 17. In some embodiments, the plurality of valve leaflets 22 may be attached and/or secured to the expandable anchor member 17 at a plurality of locations within the lumen of the replacement heart valve implant 16 and/or the expandable anchor member 17. In some embodiments, the plurality of valve leaflets 22 may be attached and/or secured to the expandable anchor member 17 using sutures, adhesives, or other suitable means.

In some embodiments, the plurality of valve leaflets 22 may include or comprise two leaflets, three leaflets, four leaflets, etc. as desired. For example, the plurality of valve leaflets 22 may comprise a first valve leaflet, a second valve leaflet, a third valve leaflet, etc. and may be referred to collectively as the plurality of valve leaflets 22. The plurality of valve leaflets 22 of the replacement heart valve implant 16 may be configured to move between an open configuration permitting antegrade fluid flow through the replacement heart valve implant 16 and/or the lumen of the replacement heart valve implant 16 and/or the expandable anchor member 17, and a closed configuration preventing retrograde fluid flow through the replacement heart valve implant 16 and/or the lumen of the replacement heart valve implant 16 and/or the expandable anchor member 17. The plurality of valve leaflets 22 may each have a free edge, wherein the free edges of the plurality of valve leaflets 22 coapt within the replacement heart valve implant 16, the expandable anchor member 17, and/or the lumen extending through the replacement heart valve implant 16 and/or the expandable anchor member 17 in the closed configuration. Some examples of suitable but non-limiting materials for the plurality of valve leaflets 22 may include bovine pericardial, polymeric materials, or other suitably flexible biocompatible materials The replacement heart valve implant 16 may include a replacement heart valve commissure assembly disposed within the lumen of the replacement heart valve implant 16 and/or the expandable anchor member 17. In some embodiments, the replacement heart valve implant 16 may include more than one replacement heart valve commissure assembly. For example, each adjacent pair of valve leaflets 22 may form and/or define one replacement heart valve commissure assembly. Therefore, the number of replacement heart valve commissure assemblies may be directly related to the number of valve leaflets 22 (e.g., three valve leaflets form and/or define three replacement heart valve commissure assemblies, two valve leaflets form and/or define two replacement heart valve commissure assemblies, etc.).

In some embodiments, the replacement heart valve implant 16 and/or the replacement heart valve commissure assembly may include a locking mechanism 70 configured to lock the expandable anchor member 17 in the "deployed" configuration. In some embodiments, the replacement heart valve implant 16 may include or comprise a plurality of locking mechanisms 70 (e.g., two locking mechanisms 70, three locking mechanisms 70, etc.). In some embodiments, each replacement heart valve commissure assembly may correspond to and/or include one corresponding locking mechanism 70. Each locking mechanism 70 may include a first locking portion or a post member 72 secured to the expandable anchor member 17 and configured to engage with a second locking portion or a buckle member 74 secured to the expandable anchor member 17, as will be described in more detail below.

In some embodiments, the actuator element 15 may be configured to releasably engage the locking mechanism 70 and/or reversibly actuate the expandable anchor member 17 and/or the replacement heart valve implant 16 between the "delivery" configuration and the "deployed" configuration and/or the "released" configuration while the actuator element 15 is engaged with the locking mechanism 70. In some embodiments, one actuator element 15 may correspond to, engage with, and/or actuate one locking mechanism 70. In some embodiments, one actuator element 15 may correspond to, engage with, and/or actuate more than one locking mechanism 70. Other configurations are also contemplated.

In some embodiments, the actuator element 15 may include a proximal end and a distal end. In use, the proximal end may be operatively connected to the handle 18, and/or manipulated or otherwise actuated by a user using the handle 18, to reversibly shift the replacement heart valve implant 16 between the "delivery" configuration and the "deployed" configuration. For example, the control knob 19 rotatable relative to a handle housing may be actuatable and/or rotatable to manipulate or otherwise actuate the actuator element 15, the outer sheath 12, and/or the inner shaft or catheter 14. In some embodiments, the actuator element 15 may be axially translatable relative to the first locking portion or post member 72 and/or the second locking portion or buckle member 74 of the replacement heart valve implant 16.

In some embodiments, the proximal end of the actuator element 15 (each actuator element 15, etc.) may be operatively connected to a central shaft extending distally from the handle 18 within the inner shaft or catheter 14. The central shaft may be actuated and/or translated by the handle 18 and/or a mechanism disposed within the handle 18 responsive to the control knob 19. In some embodiments, the actuator element 15 (each actuator element 15, etc.) may extend distally from the handle 18 within the inner shaft or catheter 14.

In some embodiments, the replacement heart valve implant 16 may include a seal member 20 (shown partially cutaway) disposed on and/or around at least a portion of the outer surface of the expandable anchor member 17. In some embodiments, the seal member 20 may be attached and/or secured to the distal or inflow end of the expandable anchor member 17 and/or the replacement heart valve implant 16, and/or the seal member 20 may be attached and/or secured to the plurality of valve leaflets 22 proximate the distal or inflow end of the expandable anchor member 17 and/or the replacement heart valve implant 16. The seal member 20 may be sufficiently flexible and/or pliable to conform to and/or around native valve leaflets and/or the native heart valve in the deployed configuration, thereby sealing an exterior of the replacement heart valve implant 16 and/or the expandable anchor member 17 within and/or against the native heart valve and/or the native valve leaflets and preventing leakage around the replacement heart valve implant 16 and/or the expandable anchor member 17.

In some embodiments, the seal member 20 may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other suitable polymeric materials are also contemplated, some of which are discussed below.

During delivery, the replacement heart valve implant 16 and/or the expandable anchor member 17 may be secured at the distal end of the inner shaft or catheter 14 by a coupler 76 coupled with a projecting portion 108 (e.g., FIG. 7) at a proximal end of the second locking portion or buckle member 74 and being held in place with a collar 80 disposed over the connection. In some embodiments, each finger 78 may include a collar 80 slidably disposed on and/or about its respective finger 78 and the projecting portion 108 of its respective second locking portion or buckle member 74. The collar 80 may be configured to maintain engagement of its respective finger 78 with one of the plurality of locking mechanisms 70 and/or the second locking portion or buckle member 74 in an interlock position. As there may be a plurality of second locking portions or buckle members 74 in the plurality of locking mechanisms 70, there may likewise be a plurality of collars 80 securing the replacement heart valve implant 16 and/or the expandable anchor member 17 to the coupler 76. The coupler 76 may include a proximal ring 77 fixedly attached to the distal end of the inner shaft or catheter 14 and a plurality of fingers 78 extending distally from the proximal ring 77. In at least some embodiments, the plurality of fingers 78 may be integrally formed with the proximal ring 77 as a single, unitary structure. The plurality of fingers 78 may be releasably coupled to the second locking portion or buckle members 74 of the plurality of locking mechanisms 70 by the plurality of collars 80. Some suitable but non-limiting materials for the coupler 76, the proximal ring 77, the plurality of fingers 78, and/or the collar 80, for example shape memory materials, metallic materials, and/or polymeric materials, are described below.

The delivery device 11 may include a stop element 86 configured to selectively prevent disengagement of the plurality of locking mechanisms 70 from the plurality of fingers 78 by maintain the plurality of collars 80 in the interlock position. The stop element 86 may include a proximal band 87 slidably disposed about the inner shaft or catheter 14 proximal of the distal end of the inner shaft or catheter 14 and a plurality of arms 88 extending distally from the proximal band 87. In some embodiments, the proximal band 87 of the stop element 86 may be positioned proximal of the proximal ring 77 of the coupler 76. In some embodiments, the proximal band 87 is positioned proximal of the distal end of the outer sheath 12 when the outer sheath 12 is disposed in the second position. Some suitable but non-limiting materials for the stop element 86, the proximal band 87, and/or the plurality of arms 88, for example shape memory materials, metallic materials, and/or polymeric materials, are described below.

In at least some embodiments, the plurality of arms 88 may be integrally formed with the proximal band 87 as a single, unitary structure. Each of the plurality of arms 88 may include a distal loop 89 disposed at a distal end of its respective arm 88, each distal loop 89 being slidably engaged with one of the plurality of fingers 78. For example, one of the plurality of fingers 78 may be slidably disposed within each or one distal loop 89. At least one of the plurality of arms 88 may include a wing element 90 configured to selectively engage with a distal end, a distal edge, and/or a distal face of the proximal ring 77 of the coupler 76. The stop element 86 may be configured to selectively prevent disengagement of the plurality of locking mechanisms 70 from the plurality of fingers 78 by maintain the plurality of collars 80 in the interlock position when the wing element 90 of the plurality of arms 88 of the stop element 86 is engaged with the proximal ring 77 of the coupler 76. Engagement of the wing element 90 with the distal end, the distal edge, and/or the distal face of the proximal ring 77 of the coupler 76 may prevent sliding movement of each distal loop 89 with respect to the plurality of fingers 78 and/or the plurality of collars 80.

The plurality of arms 88 may be biased radially outward from the inner shaft or catheter 14. In some embodiments, the plurality of arms may be self-biased radially outward from the inner shaft or catheter 14. A proximal portion of the plurality of arms 88 may be configured to shift radially relative to the inner shaft or catheter 14 between an engagement position (e.g., FIG. 2) and a disengagement position (e.g., FIG. 6), which will be explained in more detail below. In some embodiments, proximal and distal portions of the plurality of arms 88 may be generally defined and/or separated by the wing element 90. The outer sheath 12 may urge the proximal portion of the plurality of arms 88 toward the engagement position when the distal end of the outer sheath 12 is disposed over and/or distal of the proximal portion of the plurality of arms 88. As seen in FIG. 2, in the engagement position, the proximal portion of the plurality of arms 88 may be disposed adjacent to an outer surface of the inner shaft or catheter 14. In some embodiments, in the engagement position, the proximal portion of the plurality of arms 88 may be disposed generally parallel to the outer surface of the inner shaft or catheter 14. The wing element 90 may be configured to engage with the distal end, the distal edge, and/or the distal face of the proximal ring 77 of the coupler 76 in the engagement position, thereby preventing proximal movement of the plurality of arms 88, the distal loops 89 and/or the plurality of collars 80 relative to the distal end of the inner shaft or catheter 14 and/or the coupler 76, the proximal ring 77, and/or the plurality of fingers 78.

In some embodiments, the stop element 86, the proximal band 87, the plurality of arms 88, and/or the distal loops 89 may be disposed entirely proximal of the replacement heart valve implant 16, the expandable anchor member 17, the locking mechanisms 70, the first locking portion or post member 72, and/or the second locking portion or buckle member 74. In some embodiments, the stop element 86, the proximal band 87, the plurality of arms 88, and/or the distal loops 89 may not extend into or through any portion of the replacement heart valve implant 16.

In some embodiments, a tubular guide member (not shown) may be disposed over a distal portion of each of the plurality of arms 88 and/or the plurality of fingers 78 proximal of the slidable collar 80 and may serve to keep the distal portion of the plurality of arms 88 and/or the plurality of fingers 78 of the coupler 76 associated with their respective actuator element 15 extending adjacent to (and axially slidable relative to) the plurality of arms 88 and/or the plurality of fingers 78 of the coupler 76.

Figure 3:
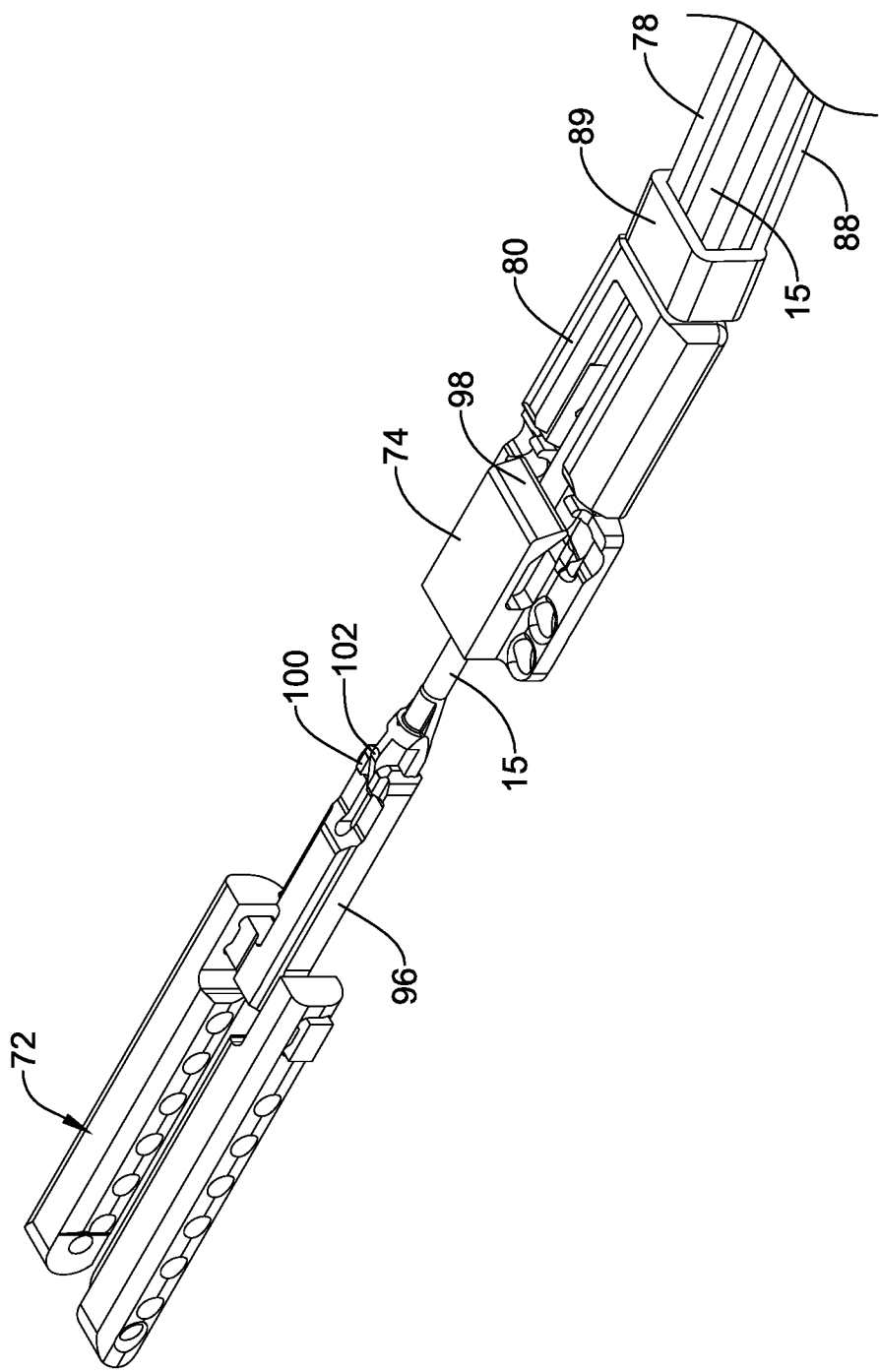
FIG. 3 illustrates selected elements of an example replacement heart valve implant in a delivery configuration and/or the engagement position.
Figure 4:
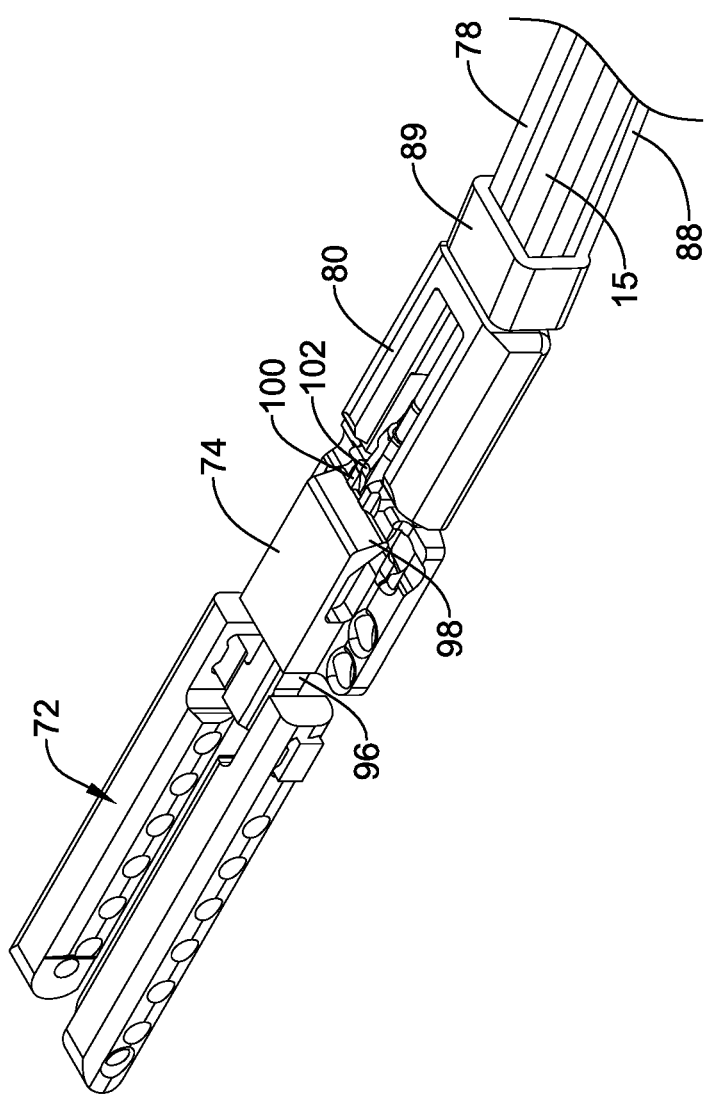
FIG. 4 illustrates selected elements of an example replacement heart valve implant in the deployed configuration and/or the engagement position.

In use, after the replacement heart valve implant 16 and/or the expandable anchor member 17 is advanced within the anatomy to the area of interest, the control knob 19, the handle 18, and/or the actuator element 15 can be used to actuate the replacement heart valve implant 16 and/or the expandable anchor member 17 from the "delivery" configuration to the "deployed" configuration by proximally retracting the actuator element 15 relative to the second locking portion or buckle member 74 and/or the expandable anchor member 17, thereby pulling the first locking portion or post member 72 into engagement with the second locking portion or buckle member 74, as discussed below with respect to FIGS. 3 and 4.

FIGS. 3 and 4 (as well as FIGS. 7 and 8) illustrate selected components and/or details of an example locking mechanism 70 and/or certain components related to the locking mechanism 70, and the general operation of those components. For simplicity and clarity purposes, only one finger 78, only one arm 88, only one actuator element 15, only one first locking portion or post member 72, and only one second locking portion or buckle member 74 are shown and discussed (the whole replacement heart valve implant 16 and/or the expandable anchor member 17 is not shown to facilitate understanding of the locking mechanism(s) 70). However, it will be understood that the following discussion may apply equally to any and/or all of the components for which there are more than one within the replacement heart valve implant 16 (i.e., the actuator elements 15, the second locking portions or buckle members 74, the first locking portions or post members 72, etc.), the delivery device 11, and/or the medical device system 10.

In some embodiments, the actuator element 15 (e.g., each actuator element 15, etc.) includes an elongated rod having a flattened distal portion and a ramp 102 (e.g., FIG. 3) extending longitudinally and/or radially outward from the actuator element 15 such that the ramp 102 has a greater outer extent than the elongated rod. The ramp 102 may be positioned proximate to and/or at a proximal end of the flattened distal portion of the actuator element 15.

In some embodiments, the flattened distal portion of the actuator element 15 may be aligned with and/or releasably coupled to the first locking portion or post member 72. In some embodiments, the flattened distal portion of the actuator element 15 may be slidably received within a longitudinally-oriented passageway of the first locking portion or post member 72, as discussed below. The handle 18 may be configured to actuate and/or translate the actuator element 15 (e.g., each actuator element 15, etc.) relative to the outer sheath 12, the replacement heart valve implant 16, the corresponding locking mechanism(s) 70 (e.g., the plurality of locking mechanisms 70, etc.), and/or the first locking portion or post member 72 in the "delivery" and/or "deployed" configuration. The actuator element 15 may be axially and/or slidably translatable through and/or relative to the distal loop 89, the collar 80, and/or the second locking portion or buckle member 74.

In some embodiments, the actuator element 15 and/or the elongated rod may be generally round, oblong, ovoid, rectangular, polygonal (e.g., two-sided, three-sided, four-sided, five-sided, six-sided, etc.) and/or combinations thereof in shape. Other shapes, both regular and irregular, are also contemplated. In some embodiments, the actuator element 15 may be formed from a single piece of wire, round stock, or other suitable material, as discussed herein. In some embodiments, the actuator element 15 may be formed by further processing the single piece of wire, round stock, or other suitable material, such as by machining, stamping, laser cutting, etc. Some suitable but non-limiting materials for the actuator element 15, the elongated rod, the flattened distal portion, and/or the ramp, for example metallic materials or polymeric materials, are described below.

In some embodiments, the first locking portion or post member 72 and the second locking portion or buckle member 74 may be longitudinally movable relative to each other along an inner surface of the expandable anchor member 17 in the "delivery" configuration and/or the "deployed" configuration. In some embodiments, the first locking portion or post member 72 may be non-releasably secured to a distal portion and/or proximate the distal or upstream end of the expandable anchor member 17 along the inner surface of the expandable anchor member 17. In some embodiments, the second locking portion or buckle member 74 may be fixedly secured to a proximal portion and/or proximate the proximal or downstream end of the expandable anchor member 17 against the inner surface of the expandable anchor member 17. The second locking portion or buckle member 74 may be configured to slidably receive at least a portion of the first locking portion or post member 72 therein. Additional discussion regarding the relative motion of these elements is provided below.

In at least some embodiments, the first locking portion or post member 72 may include an elongated proximal portion 96, and a pair of elongate legs coupled to and extending distally from a transverse distal portion (e.g., T-bar) or other coupling element at a distal end of the elongated proximal portion 96. In at least some embodiments, the transverse distal portion may be integrally formed with the elongated proximal portion 96. In some embodiments, the first locking portion or post member 72 may be formed as a single unitary structure, wherein the elongated proximal portion 96, the transverse distal portion, and/or the pair of elongate legs are integrally formed with each other and/or from a single piece of material. In some embodiments, the pair of elongate legs may secure two of the plurality of valve leaflets 22 together to form the replacement heart valve commissure assembly. Other configurations are also contemplated, and in some embodiments, the pair of elongate legs is not necessarily required to form a replacement heart valve commissure assembly or the first locking portion or post member 72.

In some embodiments, the elongated proximal portion 96 of the first locking portion or post member 72 may include a longitudinally-oriented passageway extending at least partially through the elongated proximal portion 96 of the first locking portion or post member 72, wherein the flattened distal portion of the actuator element 15 is configured to slidably engage the longitudinally-oriented passageway of the elongated proximal portion 96 of the first locking portion or post member 72. In some embodiments, the longitudinally-oriented passageway may extend completely through the elongated proximal portion 96 of the first locking portion or post member 72. In some embodiments, a longitudinal axis of the longitudinally-oriented passageway and/or the elongated proximal portion 96 of the first locking portion or post member 72 may be arranged generally parallel to the central longitudinal axis of the expandable anchor member 17 and/or the replacement heart valve implant 16.

The longitudinally-oriented passageway may be configured to slidably receive the flattened distal portion of the actuator element 15. The longitudinally-oriented passageway may include an internal cross-sectional shape or profile corresponding to an external cross-sectional shape or profile of the flattened distal portion of the actuator element 15. In some embodiments, the flattened distal portion of the actuator element 15 may be slidably disposed within the longitudinally-oriented passageway and/or may be releasably coupled to the first locking portion or post member 72 by a pinless securement feature, for example. In some embodiments, the elongated proximal portion 96 may include at least one aperture extending through a wall of the elongated proximal portion and into the longitudinally-oriented passageway, wherein the at least one aperture is configured to engage the pinless securement feature of the flattened distal portion of the actuator element 15. In some embodiments, at least a portion of the flattened distal portion of the actuator element 15 may extend into the longitudinally-oriented passageway when the flattened distal portion of the actuator element 15 is engaged with the longitudinally-oriented passageway of the elongated proximal portion 96 of the first locking portion or post member 72, for example in the elongated "delivery" configuration and/or the "everted" configuration.

In some embodiments, the flattened distal portion of the actuator element 15 may include the pinless securement feature. The pinless securement feature does not require the flattened distal portion of the actuator element 15 to be directly secured to the elongated proximal portion 96 of the first locking portion or post member 72 by a separate locking pin or other securing member, in order to secure the replacement heart valve implant 16 to the delivery device 11. Some examples of a pinless securement feature may include at least one projection configured to extend into the at least one aperture of the elongated proximal portion 96 of the first locking portion or post member 72, or at least one flexible leg configured to extend into the at least one aperture of the elongated proximal portion 96 of the first locking portion or post member 72. In some embodiments, the pinless securement feature may include a threaded feature configured to rotatable engage mating threads formed in and/or on the elongated proximal portion 96 of the first locking portion or post member 72.

In some embodiments, the first locking portion or post member 72 may be disposed within the lumen of the replacement heart valve implant 16 and/or the expandable anchor member 17 proximate the distal or inflow end of the replacement heart valve implant 16 and/or the expandable anchor member 17 when the expandable anchor member 17 is in the elongated "delivery" configuration and/or the "everted" configuration. In some embodiments, at least a portion of the first locking portion or post member 72 may be disposed distal of the expandable anchor member 17 when the expandable anchor member 17 is in the elongated "delivery" configuration and/or the "everted" configuration.

In some embodiments, a first leg of the first locking portion or post member 72 and a second leg of the first locking portion or post member 72 may be laterally and/or circumferentially spaced apart from each other to define a longitudinally-oriented tissue slot extending through the first locking portion or post member 72 in a radial direction relative to the central longitudinal axis of the replacement heart valve implant 16 and/or the expandable anchor member 17. In some embodiments, a length of the longitudinally-oriented tissue slot may extend and/or may be oriented generally parallel with the central longitudinal axis of the expandable anchor member 17 and/or the replacement heart valve implant 16.

In some embodiments, the elongated proximal portion 96 of the first locking portion or post member 72 may include a transversely-oriented depression and/or ridge 100 proximate a proximal end of the elongated proximal portion 96. As will be explained further below, the transversely-oriented depression and/or ridge 100 of the elongated proximal portion 96 may be configured to engage a transversely-oriented ridge of the second locking portion or buckle member 74 to lock the replacement heart valve implant 16 and/or the expandable anchor member 17 in the "deployed" configuration.

In some embodiments, the elongated proximal portion 96 of the first locking portion or post member 72 may include a keying or orienting shape formed in and/or extending longitudinally along a length and/or an outer surface of the elongated proximal portion 96 of the first locking portion or post member 72. In some embodiments, the keying or orienting shape may extend along an entire length of the elongated proximal portion 96 of the first locking portion or post member 72. The keying or orienting shape may serve as an alignment and/or anti-rotation feature with respect to the second locking portion or buckle member 74. For example, the keying or orienting shape may prevent relative rotation between the first locking portion or post member 72 and the second locking portion or buckle member 74 when the elongated proximal portion 96 of the first locking portion or post member 72 is engaged with the second locking portion or buckle member 74. Some suitable but non-limiting materials for the first locking portion or post member 72, for example metallic materials or polymeric materials, are described below.

The second locking portion or buckle member 74 may include a base portion having a longitudinal axis extending between a proximal end and a distal end of the second locking portion or buckle member 74. The second locking portion or buckle member 74 may include a body portion fixedly attached to and/or integrally formed with the base portion, the body portion defining a longitudinal channel extending through the body portion of the second locking portion or buckle member 74. In at least some embodiments, the longitudinal channel may be oriented substantially parallel with the longitudinal axis of the base portion. In some embodiments, at least a part of the body portion may extend away from a distal portion of a top surface of the base portion. For example, the body portion may extend radially inward from the base portion relative to the central longitudinal axis of the replacement heart valve implant 16 and/or the expandable anchor member 17.

In some embodiments, the body portion of the second locking portion or buckle member 74 may include a flap portion 98 extending proximally and/or toward the proximal end of the base portion from the body portion. In some embodiments, the flap portion 98 may include a transversely-oriented ridge extending toward the base portion and laterally across the base portion, such that when the second locking portion or buckle member 74 is viewed along the longitudinal axis of the base portion, the transversely-oriented ridge obstructs at least a portion of the longitudinal channel. In some embodiments, the body portion and/or the flap portion 98 of the second locking portion or buckle member 74 may include at least one hole or aperture formed therein for attaching a radiopaque marker to the second locking portion or buckle member 74 to aid in visualization of the second locking portion or buckle member 74.

The flap portion 98 may be configured to deflect radially relative to the central longitudinal axis of the expandable anchor member 17 and/or the replacement heart valve implant 16. The ramp 102 of the actuator element 15 may be configured to deflect the flap portion 98 of the second locking portion or buckle member 74 radially inward as the ramp (and the first locking portion or post member 72 engaged thereto) is longitudinally translated through the longitudinal channel of the body portion of the second locking portion or buckle member 74. In some embodiments, the flap portion 98 may be biased or self-biased toward a neutral position aligned with the body portion and/or may be biased or self-biased into the longitudinal channel and/or toward the base portion of the second locking portion or buckle member 74.

In some embodiments, the second locking portion or buckle member 74 may include the projecting portion 108 (e.g., FIG. 7) at a proximal end of the base portion of the second locking portion or buckle member 74, the projecting portion 108 being configured to releasably attach the replacement heart valve implant 16 to the delivery device 11 and/or the plurality of fingers 78 of the coupler 76 via the collar 80. In at least some embodiments, the longitudinal channel may have a keyed, directional, or non-round cross-sectional profile or shape configured to slidably receive the elongated proximal portion 96 of the first locking portion or post member 72. The first locking portion or post member 72 may have an external cross-sectional profile or shape corresponding to the keyed, directional, or non-round internal cross-sectional profile or shape of the longitudinal channel. As such, the first locking portion or post member 72 may be non-rotatable relative to the second locking portion or buckle member 74 when the elongated proximal portion 96 of the first locking portion or post member 72 is engaged with and/or at least partially disposed within the longitudinal channel of the second locking portion or buckle member 74. Some suitable but non-limiting materials for the second locking portion or buckle member 74, for example metallic materials or polymeric materials, are described below.

During delivery, the replacement heart valve implant 16 may be secured at the distal end of the coupler 76 and/or the inner shaft or catheter 14 by two elongated tines 104 (e.g., FIG. 7) of the finger 78 of the coupler 76 being matingly coupled with the projecting portion 108 of the second locking portion or buckle member 74 by the collar 80, and by the actuator element 15 being coupled to its corresponding first locking portion or post member 72, for example by the pinless securement feature. When the replacement heart valve implant 16 is advanced within the anatomy to the area of interest, the outer sheath 12 may be translated and/or actuated proximally to expose the replacement heart valve implant 16. As can be appreciated, a proximal end of the first locking portion or post member 72 and a distal end of the second locking portion or buckle member 74 may be longitudinally separated and/or spaced apart in the "delivery" configuration, as seen in FIG. 3 for example. In at least some embodiments, the first locking portion or post member 72 may be longitudinally actuatable and/or translatable relative to the second locking portion or buckle member 74 in the "delivery" configuration, and/or between the "delivery" configuration and the "deployed" configuration.

Then, the actuator element 15 can be actuated (e.g., proximally retracted) to axially shorten and/or radially expand the replacement heart valve implant 16 and/or the expandable anchor member 17 from the "delivery" configuration toward the "deployed" configuration by proximally retracting and/or translating the actuator element 15 to pull the first locking portion or post member 72 into engagement with the second locking portion or buckle member 74, as seen in FIG. 4, using the handle 18 and/or the control knob 19 for example.

As the first locking portion or post member 72 is actuated and/or translated proximally through and/or relative to the second locking portion or buckle member 74, the transversely-oriented depression and/or ramp 102 proximate the proximal end of the elongated proximal portion 96 engages the transversely-oriented ridge of the flap portion 98 of the second locking portion or buckle member 74 to lock the expandable anchor member 17 and/or the replacement heart valve implant 16 into the "deployed" configuration, as seen in FIG. 4. Engagement of the transversely-oriented depression and/or ramp 102 proximate the proximal end of the elongated proximal portion 96 and the transversely-oriented ridge of the flap portion 98 of the second locking portion or buckle member 74 may limit or prevent distal movement and/or axial translation of the first locking portion or post member 72 relative to the second locking portion or buckle member 50 in the "deployed" configuration after the actuator element 15 has been disengaged from the locking mechanism 70 and/or the first locking portion or post member 72. Following locking of the expandable anchor member 17 and/or the replacement heart valve implant 16 in the "deployed" configuration, positioning of the replacement heart valve implant 16 may be verified using a suitable imaging technique.

In some embodiments and/or some procedures, it may be desirable to remove and/or reposition the replacement heart valve implant 16 and/or expandable anchor member 17. To do so, a clinician may urge and/or translate the actuator element 15 in a second (e.g., distal) direction to extend and/or elongate the expandable anchor member 17 back towards the "delivery" configuration. Axial translation of the actuator element 15 in the second (e.g., distal) direction relative to the locking mechanism 70 (e.g., the first locking portion or post member 72 and/or the second locking portion or buckle member 74) may slidably engage the ramp 102 of the actuator element 15 with the flap portion 98 and/or the transversely-oriented ridge of the flap portion 98 the second locking portion or buckle member 74, thereby deflecting the flap portion 98 of the second locking portion or buckle member 74 away from the longitudinal channel of the second locking portion or buckle member 74 and/or the actuator element 15 and/or radially inward relative to the central longitudinal axis of the expandable anchor member 17, and permitting the first locking portion or post member 72 to pass back through and/or out of the longitudinal channel of the second locking portion or buckle member 74, thereby shifting the replacement heart valve implant 16 back towards the "delivery" configuration.

Figure 5:
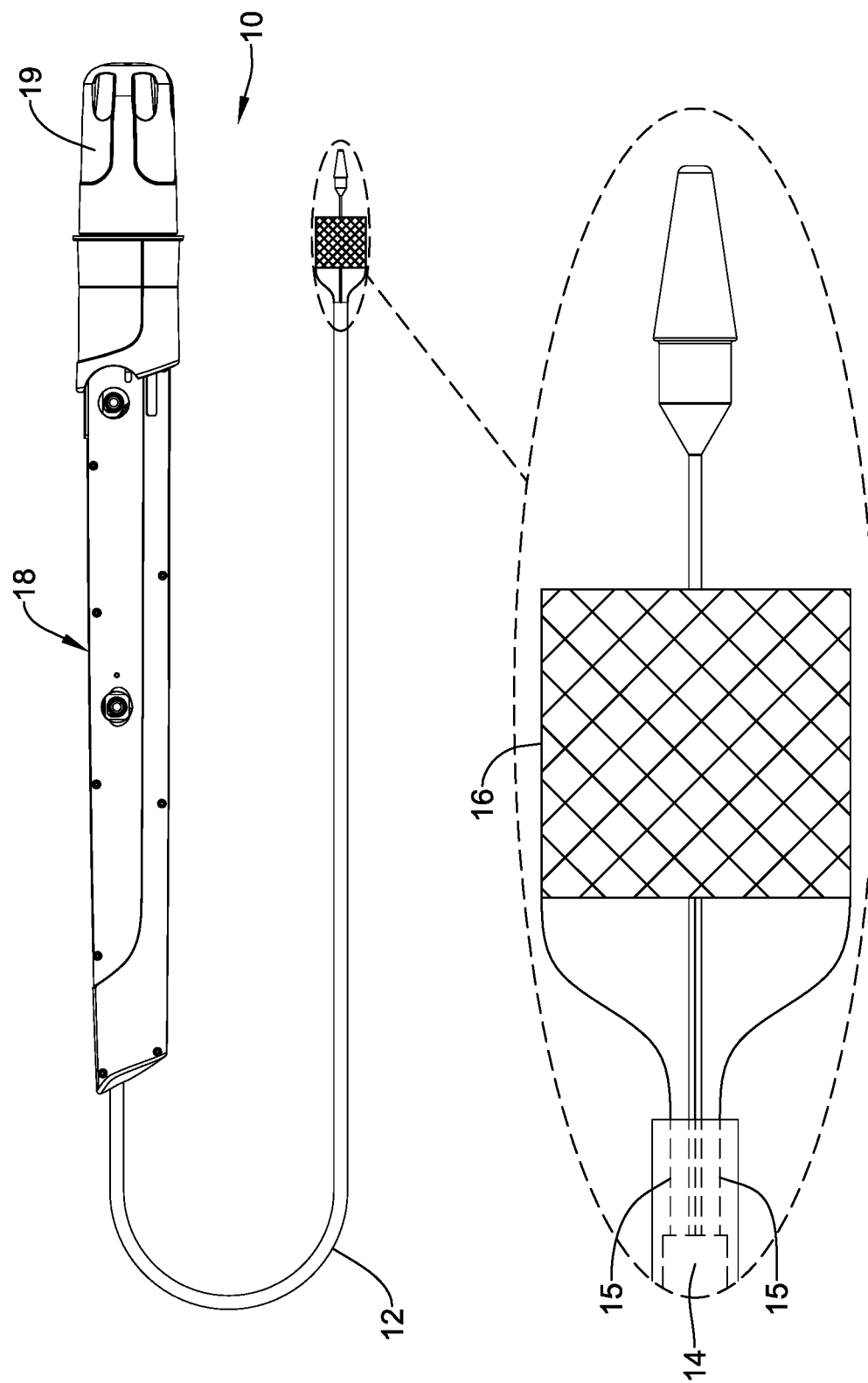
FIG. 5 illustrates an example medical device system in the deployed configuration.
Figure 6:
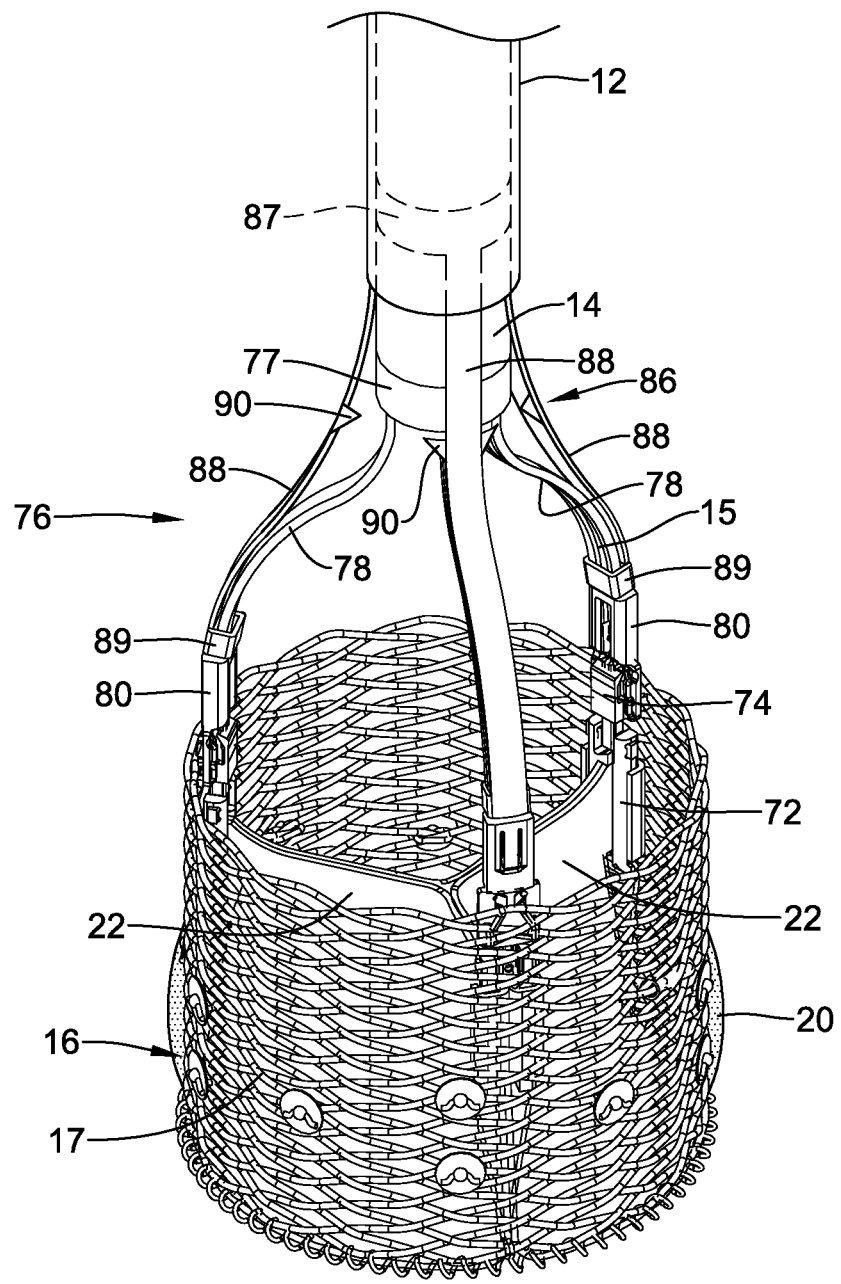
FIG. 6 is a perspective view of selected elements of the medical device system in the deployed configuration and/or a disengagement position.

After verifying satisfactory placement of the replacement heart valve implant 16, such as by an appropriate imaging technique, the locking pin 13 may be removed from the handle 18, as seen in FIG. 5, and the control knob 19 may be rotated and/or actuated to retract the outer sheath 12 to the second position relative to the inner shaft or catheter 14 and/or the coupler 76, as seen in FIG. 6. At any point prior to the removal of the locking pin 13, the replacement heart valve implant 16 may be repositioned and/or redeployed as discussed above.

Removal of the locking pin 13 may permit the outer sheath 12 to be shifted to the second position relative to the inner shaft or catheter 14 and/or the stop element 86, thereby exposing the proximal portion of the plurality of arms 88. Proximal retraction of the outer sheath 12 relative to the inner shaft or catheter 14 and/or the proximal band 87 of the stop element 86 may permit the proximal portion of the plurality of arms 88 to shift toward the disengagement position.

As discussed herein, the plurality of arms 88 may be biased or self-biased to expand and/or shift radially outward relative to the inner shaft or catheter 14. Therefore, when the plurality of arms 88, and in particular the proximal portion of the plurality of arms 88, is unconstrained by the outer sheath 12, the plurality of arms 88 may be configured to shift toward and/or into the disengagement position, as seen in FIG. 6. In some embodiments, proximal retraction of the outer sheath 12 relative to the inner shaft or catheter 14 and/or the proximal band 87 of the stop element 86 may permit the stop element 86 to disengage from the proximal ring 77 of the coupler 76. In the disengagement position, the proximal portion of the plurality of arms 88 may extend radially outward from the outer surface of the inner shaft or catheter 14 at an oblique angle. In the disengagement position, the wing element 90 is radially spaced apart from the proximal ring 77. When the stop element 86 is disengaged from the proximal ring 77 of the coupler 76, the plurality of collars 80 may be slidable relative to the plurality of fingers 78 to a release position. In the disengagement position, the wing element 90 may no longer prevent sliding movement of the collar 80 relative to its respective finger 78.

Figure 7:
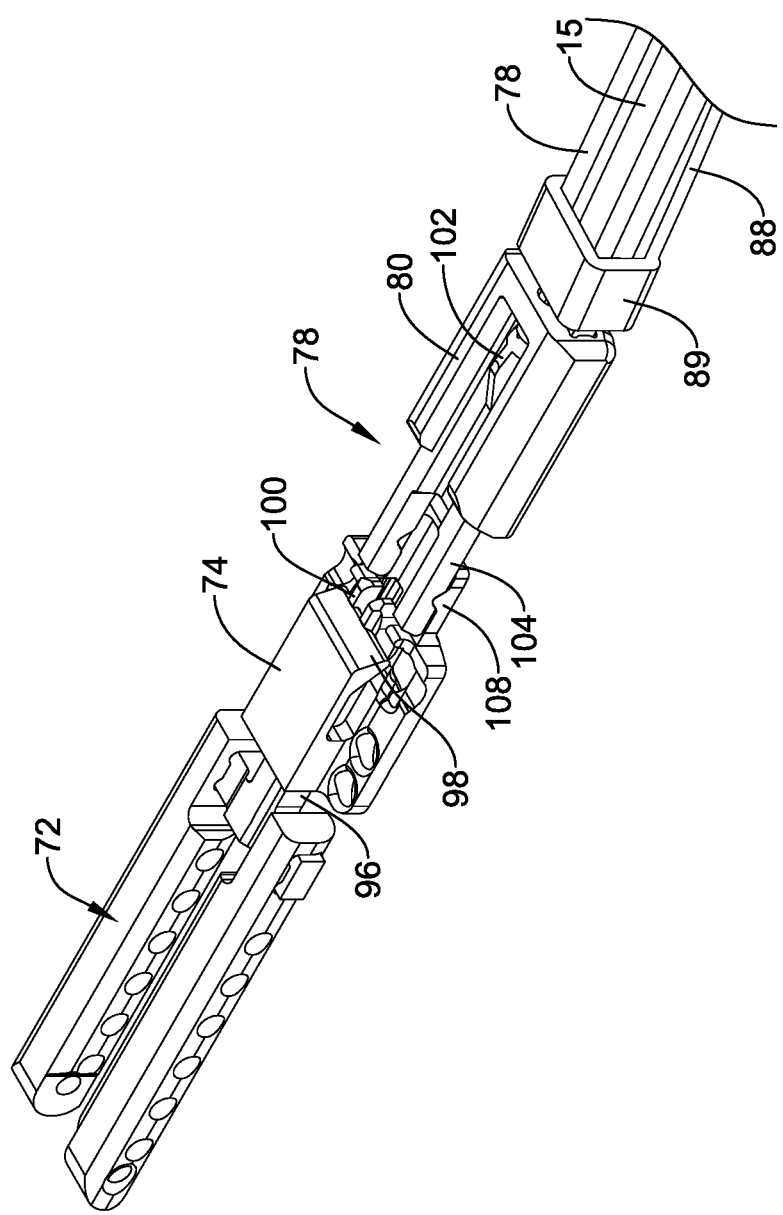
FIG. 7 illustrates selected elements of an example replacement heart valve implant in the deployed configuration and/or the disengagement position.
Figure 8:
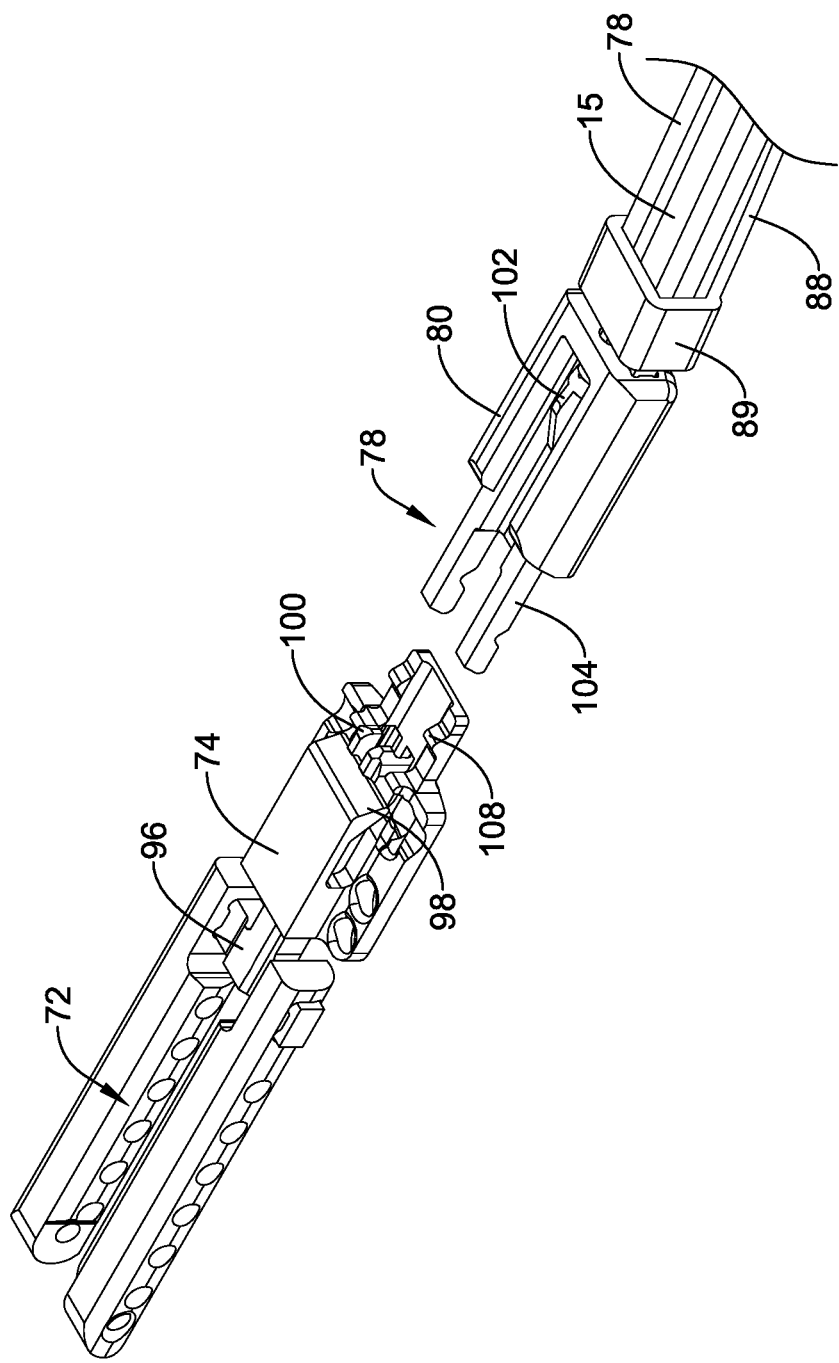
FIG. 8 illustrates selected elements of an example replacement heart valve implant in the released configuration and/or the disengagement position.

Next, with the proximal portion of the plurality of arms 88 of the stop element 86 shifted into the disengagement position, the flattened distal portion of the actuator element 15 may be permitted to be pulled proximally out of the first locking portion or post member 72 by further rotation of the control knob 19, causing the ramp 102 to subsequently engage the collar 80 and thereby retract the collar 80 from the two elongated tines 104 and the projecting portion 108 to the release position, as seen in FIG. 7, as well as shift the distal loop 89 proximally, which may also shift and/or slide the proximal band 87 proximally along the inner shaft or catheter 14. Once the locking pin 13 has been removed, the outer sheath 12 shifted to the second position relative to the inner shaft or catheter 14, and the control knob 19 further rotated to retract the flattened distal portion of the actuator element 15 proximally out of the first locking portion or post member 72, the replacement heart valve implant 16 may not be repositionable. After the collar 80 has been retracted to the release position, the two elongated tines 104 may decouple from the projecting portion 108, as seen in FIG. 8, and the finger 78 of the coupler 76 may be withdrawn from the replacement heart valve implant 16 thereby leaving the replacement heart valve implant 16 (and/or the expandable anchor member 17) in the anatomy at the area of interest in a "released" configuration, as seen in FIG. 9.

Figure 10:
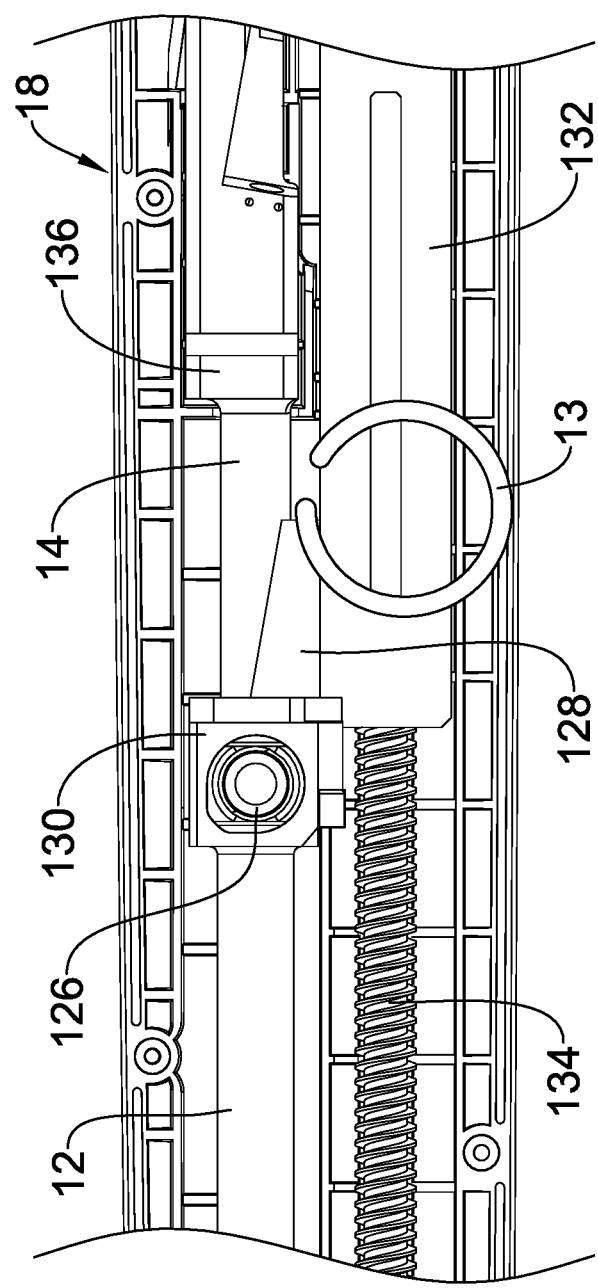
FIGS. 10-11 illustrate selected elements of a delivery device shifting between a first position and a second position.
Figure 11:
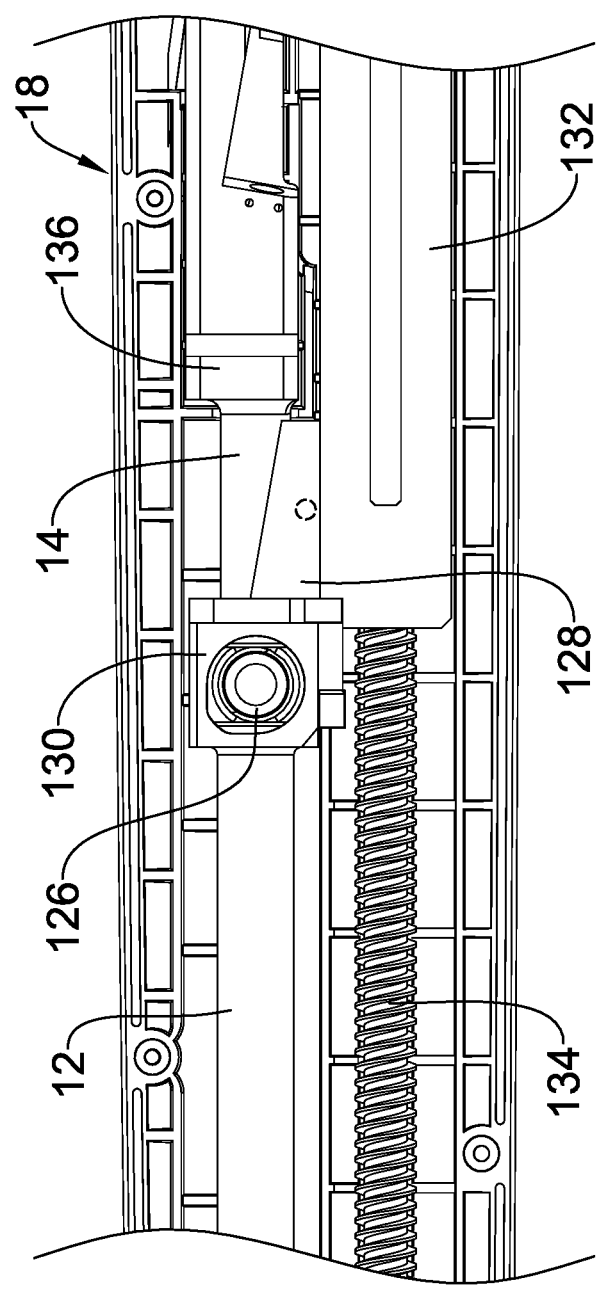

Referring back to FIG. 1, in at least some embodiments, the handle 18 may include one or more apertures and/or flush ports that can be used to flush the medical device system 10 and/or the delivery device 11. In some embodiments, the distal flush port and the proximal flush port may be accessible from an exterior of the handle 18 through the distal aperture and the proximal aperture, respectively. FIGS. 10 and 11 illustrate selected aspects of certain internal components of the medical device system 10, including the distal flush port, with a portion of the handle 18 removed for viewing.

The outer sheath 12 may be attached to a sheath adapter 130. The sheath adapter 130 may attached to a sheath carriage 132, which may be threaded onto a lead screw 134. The distal flush port 126 may be disposed on the sheath adapter 130. In general, the distal flush port 126 provides access to the interior or lumen of the outer sheath 12 (e.g., access to space between the inner shaft or catheter 14 and outer sheath 12) so that a clinician can flush fluid through the lumen of outer sheath 12 to remove any unwanted materials (e.g., air, fluid, contaminants, etc.) therein prior to use of the medical device system 10 and/or the delivery device 11. In some embodiments, the distal flush port 126 has a luer type connector (e.g., a one-way luer connector) that allows a device such as a syringe with a corresponding connector to be attached for flushing.

Extending through and proximally from the sheath adapter 130 is the inner shaft or catheter 14. A proximal end of the inner shaft or catheter 14 is attached (e.g., fixedly attached) to an interior body or diverter 136 that may have one or more passageways or lumens formed therein. In some embodiments, the plurality of actuator elements 15 may each extend through respective passageways. Alternatively, proximal ends of the plurality of actuator elements 15 may each be attached to a shaft or hypotube (e.g., solid in cross-section, tubular, etc.), and each of the shafts may extend through the one or more passageways.

In some embodiments, the handle 18 includes the locking pin 13 extending through the outer wall of the handle 18 and/or extending into the handle 18. As shown in FIG. 10 for example, the sheath adapter 130 may include a proximal extension 128 extending proximal from sheath adapter 130. In some embodiments, the proximal extension 128 may extend around the inner shaft or catheter 14, for example in a U-shaped configuration. In some embodiments, the proximal extension 128 may be substantially flat and/or straight. Other suitable configurations are also contemplated. The proximal extension 128 may make contact with the locking pin 13 when the replacement heart valve implant 16 has been shifted into the "deployed" configuration. At any time that the proximal extension 128 is disposed distal of the locking pin 13, the outer sheath 12 may be in the first position relative to the inner shaft or catheter 14. The locking pin 13 may prevent the outer sheath 12 from being shifted to the second position relative to the inner shaft or catheter 14 when the locking pin 13 is in place and/or extends into the handle 18 by interfering with proximal movement of the proximal extension 128. After the practitioner is satisfied with the positioning of the replacement heart valve implant 16 within the area of interest, the locking pin 13 may be removed (e.g., FIG. 5). Then the control knob 19 and/or the handle 18 may be actuated to proximally retract the outer sheath 12 to the second position relative to the inner shaft or catheter 14, as shown in FIG. 11 for example. Proximally retracting the outer sheath 12 to the second position permits the stop element 86 to shift to the disengagement position, thereafter allowing the plurality of actuator elements 15 to disengage from the plurality of locking mechanisms 70 and release the replacement heart valve implant 16 from the delivery device 11.

The materials that can be used for the various components of the medical device system 10, the outer sheath 12, the inner shaft or catheter 14, the replacement heart valve implant 16, the handle 18, etc. (and/or other systems disclosed herein) and the various elements thereof disclosed herein may include those commonly associated with medical devices. For simplicity purposes, the following discussion makes reference to the medical device system 10, the outer sheath 12, the inner shaft or catheter 14, the replacement heart valve implant 16, the handle 18, etc. However, this is not intended to limit the devices and methods described herein, as the discussion may be applied to other elements, members, components, or devices disclosed herein, such as, but not limited to, the actuator element(s) 15, the seal member 20, the plurality of valve leaflets 22, the expandable anchor member 17, the first locking portion or post member 72, the second locking portion or buckle member 74, the coupler 76, the collars 80, the stop element 86, etc., and/or elements or components thereof.

In some embodiments, the medical device system 10, the outer sheath 12, the inner shaft or catheter 14, the replacement heart valve implant 16, the handle 18, etc., and/or components thereof (such as, but not limited to, the actuator element(s) 15, the seal member 20, the plurality of valve leaflets 22, the expandable anchor member 17, the first locking portion or post member 72, the second locking portion or buckle member 74, the coupler 76, the collars 80, the stop element 86, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 10, the outer sheath 12, the inner shaft or catheter 14, the replacement heart valve implant 16, the handle 18, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 10, the outer sheath 12, the inner shaft or catheter 14, the replacement heart valve implant 16, the handle 18, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10, the outer sheath 12, the inner shaft or catheter 14, the replacement heart valve implant 16, the handle 18, etc. to achieve the same result.

In some embodiments, a degree of Magnetic Resonance Imaging (MRI) compatibility is imparted into the medical device system 10, the outer sheath 12, the inner shaft or catheter 14, the replacement heart valve implant 16, the handle 18, etc. For example, the medical device system 10, the outer sheath 12, the inner shaft or catheter 14, the replacement heart valve implant 16, the handle 18, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 10, the outer sheath 12, the inner shaft or catheter 14, the replacement heart valve implant 16, the handle 18, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 10, the outer sheath 12, the inner shaft or catheter 14, the replacement heart valve implant 16, the handle 18, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 10, the outer sheath 12, the inner shaft or catheter 14, the replacement heart valve implant 16, the handle 18, the seal member 20, etc. and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 10, the outer sheath 12, the inner shaft or catheter 14, the replacement heart valve implant 16, the handle 18, the seal member 20, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 10, the outer sheath 12, the inner shaft or catheter 14, the replacement heart valve implant 16, the handle 18, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made to details, particularly in matters of shape, size, and arrangement of steps, without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
   a delivery device including an outer sheath and an inner shaft having a coupler fixed to a distal end of the inner shaft
   wherein the coupler includes a proximal ring fixed to the distal end of the inner shaft and a plurality of fingers extending distally from the proximal ring; and
   a replacement heart valve implant releasably attached to the coupler, the replacement heart valve implant including an expandable anchor member and a plurality of locking mechanisms configured to engage with the coupler;
   wherein the delivery device includes a plurality of collars configured to secure the coupler to the plurality of locking mechanisms;
   wherein the delivery device includes a stop configured to selectively prevent disengagement of the plurality of collars from the plurality of locking mechanisms,
   wherein the stop includes a proximal band slidably disposed about the inner shaft proximal of the distal end of the inner shaft and a plurality of arms extending distally from the proximal band;
   wherein each of the plurality of arms includes a distal loop disposed at a distal end of its respective arm, each distal loop being slidably engaged with one of the plurality of fingers.

2. The medical device system of claim 1, wherein at least one of the plurality of arms includes a wing element configured to selectively engage with the proximal ring of the coupler.

3. The medical device system of claim 2, wherein engagement of the wing element with the proximal ring of the coupler prevents proximal sliding movement of each distal loop with respect to the plurality of fingers.

4. The medical device system of claim 1, wherein the plurality of arms is self-biased radially outward from the inner shaft.

5. The medical device system of claim 4, wherein a proximal portion of the plurality of arms is configured to shift radially relative to the inner shaft between an engagement position and a disengagement position.

6. The medical device system of claim 5, wherein in the engagement position, the proximal portion of the plurality of arms is disposed adjacent to an outer surface of the inner shaft, and in the disengagement position, the proximal portion of the plurality of arms is spaced radially outward from the outer surface of the inner shaft.

7. The medical device system of claim 5, wherein in the engagement position, the proximal portion of the plurality of arms is disposed generally parallel to an outer surface of the inner shaft, and in the disengagement position, the proximal portion of the plurality of arms extends radially outward from the outer surface of the inner shaft at an oblique angle.

8. The medical device system of claim 5, wherein the outer sheath urges the proximal portion of the plurality of arms toward the engagement position when a distal end of the outer sheath is a disposed over the proximal portion of the plurality of arms.

9. The medical device system of claim 8, wherein proximal retraction of the outer sheath relative to the proximal band permits the proximal portion of the plurality of arms to shift toward the disengagement position.

10. A medical device system, comprising:
a delivery device including an outer sheath and an inner shaft having a coupler fixed to a distal end of the inner shaft, wherein the coupler includes a proximal ring fixed to the distal end of the inner shaft and a plurality of fingers extending distally from the proximal ring; and
a replacement heart valve implant releasably attached to the coupler, the replacement heart valve implant including an expandable anchor member and a plurality of locking mechanisms configured to engage with the plurality of fingers;
wherein the delivery device includes a plurality of collars, wherein one collar is slidably disposed on each of the plurality of fingers and is configured to maintain engagement of its respective finger with one of the plurality of locking mechanisms in an interlock position;
wherein the delivery device includes a stop configured to selectively prevent disengagement of the plurality of locking mechanisms from the plurality of fingers by maintaining the plurality of collars in the interlock position when the stop is engaged with the proximal ring of the coupler.

11. The medical device system of claim 10, wherein proximal retraction of the outer sheath relative to the stop permits the stop to disengage the proximal ring of the coupler.

12. The medical device system of claim 11, wherein when the stop is disengaged from the proximal ring of the coupler, the plurality of collars is slidable relative to the plurality of fingers to a release position.

13. The medical device system of claim 10, wherein the stop is disposed proximal of the replacement heart valve implant.

14. The medical device system of claim 10, wherein the stop does not extend into or through any portion of the replacement heart valve implant.

\* \* \* \* \*